United States Patent [19]
Blumenhopf et al.

[11] Patent Number: 5,393,883
[45] Date of Patent: Feb. 28, 1995

[54] ANTIVIRAL COMBINATIONS AND COMPOUNDS THEREFOR

[75] Inventors: Todd A. Blumenhopf, Chapel Hill; Thomas Spector, Durham; Devron R. Averett; Robert W. Morrison, Jr., both of Raleigh; Eric C. Bigham, Chapel Hill; Virgil L. Styles, Durham, all of N.C.

[73] Assignee: Burroughs Wellcome Co., Research Triangle Park, N.C.

[21] Appl. No.: 832,228

[22] Filed: Feb. 7, 1992

Related U.S. Application Data

[62] Division of Ser. No. 371,482, Jun. 26, 1989, Pat. No. 5,175,165.

[30] Foreign Application Priority Data

Jun. 27, 1988 [GB] United Kingdom ............... 8815241

[51] Int. Cl.$^6$ ........................................... C07D 413/00
[52] U.S. Cl. ................................. 544/124; 544/265; 544/266; 546/264; 546/277; 546/331; 549/59; 549/60
[58] Field of Search .............. 514/357, 183, 210, 255, 514/262, 265, 266; 544/265, 277, 124; 549/59, 60; 546/331, 277, 264

[56] References Cited

U.S. PATENT DOCUMENTS

| | | | |
|---|---|---|---|
| 4,719,221 | 1/1988 | Morrison | 514/357 |
| 4,777,166 | 10/1988 | Smith et al. | 514/183 |
| 5,021,437 | 6/1991 | Blumenkopf | 514/357 |

*Primary Examiner*—John W. Rollins
*Assistant Examiner*—James D. Wilson
*Attorney, Agent, or Firm*—Donald Brown; Hannah O. Green

[57] ABSTRACT

The present invention relates to novel ribonucleotide reductase inhibitors and new combinations comprising an antiviral compound, such as acyclovir, and a thiocarbonohydrazone ribonucleotide reductase inhibitor for the chemotherapeutic treatment of virus infections, especially viruses of the herpes group.

6 Claims, No Drawings

ANTIVIRAL COMBINATIONS AND COMPOUNDS THEREFOR

This is a divisional of application(s) Ser. No. 07/371,482, now U.S. Pat. No. 5,175,165, filed on Jun. 26, 1989.

FIELD OF INVENTION

The present invention relates to new antiviral combinations for the chemotherapeutic treatment of virus infections, especially viruses of the herpes group, and to certain compounds for use in such combinations.

BACKGROUND INFORMATION

During the last fifteen years, various antiviral chemotherapeutic agents have been developed for clinical evaluation. A problem with the development of such agents is that, unlike bacteria, viruses are not free-living organisms and are dependent for replication on the life processes of the host cell which they are infecting. It is therefore highly desirable for the antiviral agent to exert its effect specifically on the replicative processes of the virus rather than on the corresponding processes of normal (non-infected) cells. The antiviral agents so far developed act via a variety of mechanisms to exert their antiviral effects. These mechanisms involve inhibition of different stages in the process of viral replication in the host cells.

One particular stage of replication at which the virus is susceptible to inhibition is the stage of nucleic acid replication, i.e., the production of DNA from DNA, RNA from RNA, or DNA from RNA (depending on whether the virus is a DNA or an RNA virus), where the viral DNA or RNA acts as a template for the production of new DNA or RNA. In the case of DNA viruses, the production of new viral DNA involves the interaction of the enzyme DNA polymerase with the constituent nucleotides (specifically deoxyribonucleotides) which act as building blocks for the new DNA. Antiviral action at this stage generally involves the use of "fraudulent" or deleterious nucleotides which mimic the normal vital materials and either compete for DNA polymerase and/or are incorporated into the viral DNA chain to make it non-functional.

These "fraudulent" or deleterious nucleotides comprise a triphosphate derived from a nucleoside analog which is converted by enzymes first into the monophosphate and then subsequently into the diphosphate and finally into the triphosphate. An example of this type of antiviral agent is the marketed compound, acyclovir, i.e., 9-(2-hydroxyethoxymethyl)guanine (U.S. Pat. No. 4,199,574), which contains an acyclic side-chain in the 9-position of guanine compared with a cyclic sugar residue in this position in guanosine. The antiviral mechanism of action of acyclovir is believed to involve first its conversion to acyclovir monophosphate by the enzyme thymidine kinase, which is specific to herpes-infected cells. Once formed, acyclovir monophosphate is converted by normal cellular enzymes (kinases) via the diphosphate to acyclovir triphosphate (ACV-TP). Acyclovir triphosphate is believed to serve as an inhibitor of viral DNA polymerase since it resembles the natural nucleotide substrate, deoxyguanosine triphosphate (dGTP), and as a result competes with dGTP for binding to the DNA polymerase and thus competitively inhibits the effectiveness of the enzyme and consequently viral replication. When ACV-TP acts as a substrate for DNA polymerase it becomes incorporated into the viral DNA chain, but since it lacks the 3'-hydroxyl group present on the cyclic sugar moiety of the natural nucleotide substrate, it presumably acts as a DNA chain terminator. It also apparently inactivates the viral DNA polymerase. Thus, viral replication is prevented.

The antiviral effect of acyclovir, and related compounds which operate via an analogous mode of action, is believed to involve competitive inhibition, apparent inactivation of the viral DNA polymerase, and termination of the growing DNA chain.

A disadvantageous aspect of a competitive inhibitor is that the normal substrate may accumulate and become more effective in competitively blocking the binding of the inhibitor. In this manner, the build up of, for example, dGTP may hinder the binding of ACV-TP to the polymerase and thereby prevent subsequent inhibition and termination of viral DNA processing.

European Patent Specification 135,713 (U.S. Pat. No. 4,758,572) discloses antiviral combinations of nucleoside analogs and thiosemicarbazone ribonucleotide reductase inhibitors. U.S. Pat. No. 4,719,221 discloses the thiosemicarbazones in European Patent Specification 135,713.

SUMMARY OF THE INVENTION

It has now been discovered that certain ribonucleotide reductase (RR) inhibitors, as disclosed herein, have anti-herpes virus activity. Furthermore, these RR inhibitors significantly potentiate the efficacy of antiviral compounds, such as acyclovir. The combination of RR inhibitor and antiviral compound has the effect, in virus-infected cells, of decreasing the pool of deoxynucleotide substrate of virus DNA polymerase and, surprisingly, increasing the triphosphate form of the antiviral compound. Thus, the ratio of triphosphate form of the antiviral compound to the competing deoxy-nucleotide substrate of viral DNA polymerase, such as deoxyguanosine triphosphate, is greatly improved, and the binding of the triphosphate form of the antiviral compound to the viral DNA polymerase is facilitated.

The net result is that the use of certain RR inhibitors, as disclosed herein, in combination with an antiviral compound of the above described type results in a surprising synergistic increase in antiviral efficacy in comparison with the individual antiviral effects of the components of the combination. Certain RR inhibitors of this invention are more potent in synergy with acyclovir in vivo and substantially less toxic than the thiosemicarbazone RR inhibitors cited in the above-mentioned European Patent Specification.

OBJECTS OF THE INVENTION

According to a feature of the present invention, there is provided a combination of (1) an antiviral compound which is capable of being converted in vivo, via a metabolic pathway, which includes a step dependent upon virus-induced enzyme, to an inhibitor of, or an alternative substrate for, viral DNA polymerase, and (2) a ribonucleotide reductase inhibitor which is a compound of Formula (III)

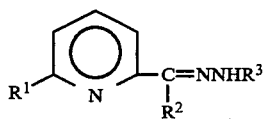 (III)

wherein $R^1$ and $R^2$ each independently represents hydrogen or $C_{1-6}$ alkyl; and $R^3$ represents a group of formula (A):

 (A)

wherein X represents oxygen or sulfur; $R^4$, and $R^5$ each independently represents hydrogen or $C_{1-6}$ alkyl; $R^6$ represents hydrogen; and $R^7$ represents $C_{1-6}$ alkyl(e.g. methyl or ethyl) substituted by a 5- or 6-membered heterocyclic ring containing at least one heteroatom selected from oxygen and nitrogen, (e.g. morpholino or pyridyl); adamantyl; aryl (e.g. phenyl or naphthyl)-$C_{1-6}$ alkyl (e.g. methyl); aroyl (e.g. phenylcarbonyl); aryl (e.g. phenyl or naphthyl); a 5- or 6-membered heterocyclic ring containing at least one heteroatom selected from oxygen and nitrogen (e.g. morpholino or pyridyl); $C_{3-8}$ cycloalkyl (e.g. cyclopentyl); or esterified carboxyl; such groups represented by $R^7$ being optionally substituted by at least one $C_{1-6}$ alkyl (e.g. methyl), $C_{1-6}$ alkoxy (e.g. methoxy), halo-$C_{1-6}$ alkyl (e.g. trifluoromethyl), mono- or di-$C_{1-6}$ alkylamino (e.g. dimethylamino), nitro, halo (e.g. chloro, bromo, fluoro, or iodo), cyano or carboxyl; or formula (B):

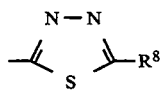 (B)

wherein $R^8$ represents a group of Formula (a):

 (a)

wherein $R^6$ and $R^7$ are defined above in Formula (A); or a group of Formula (b):

 (b)

wherein $R^9$ and $R^{10}$ together with the nitrogen atom to which they are attached form a benzimidazolidine ring substituted by a thio or oxo group in the 2-position; or a group of Formula (c):

 (c)

wherein $R^{11}$ represents hydrogen or $C_{1-6}$ alkyl; provided that when $R^1$, $R^4$, $R^5$ and $R^6$ represent hydrogen, $R^2$ represents methyl, and $R^3$ represents Formula (A), then $R^7$ is not 2-chlorophenyl; and pharmaceutically acceptable salts thereof, wherein components (1) and (2) of the combination are employed in a ratio whereby a synergistic antiviral effect is achieved. The term "synergistic antiviral effect" is used to denote an antiviral effect which is significantly greater than the purely additive effects of the individual above-defined components of the combination.

The present invention also provides the above-defined combination for use in medical therapy e.g. the treatment of viral diseases in the human and animal body. Examples of such viral diseases include those caused by viruses of the herpes family, for example, herpes simpex 1 and 2 viruses (HSV 1, HSV 2), varicella zoster virus (VZV), cytomegalovirus (CMV) and Epstein-Barr virus (EBV), but other herpes virus infections can also be treated (e.g. feline herpes virus infections).

The invention further provides a method for the treatment of vital diseases in a human or animal body which comprises administering to the human or animal body an effective non-toxic amount of a combination as defined above. It will be appreciated that, in accordance with the present invention, the antiviral compound and the RR inhibitor may be administered simultaneously (in the same or different pharmaceutical formulations) or sequentially. In the latter case, however, the components of the combination are preferably administered within a sufficiently short interval to ensure that a synergistic antiviral effect is achieved.

The invention further provides use of a combination according to the present invention in the manufacture of a medicament for use in the treatment or prophylaxis of a virus infection, particularly herpes, selected from HSV 1, HSV 2, VZV, CMV and EBV.

The present invention also provides:

a) A method of therapeutically increasing the pool size of a deleterious substrate and/or an inhibitor of viral DNA polymerase in a mammal having a viral infection and receiving an antiviral compound, which depends on viral-induced enzyme(s) for conversion to said deleterious substrate and/or inhibitor in the mammal, and the improvement of administering to said mammal an RR inhibitor of formula (III) (as defined above) or a pharmaceutically acceptable salt thereof in an amount effective for increasing the pool of said inhibitor and/or deleterious substrate of viral DNA polymerase in said mammal; and b) A method of potentiating in a mammal having a viral infection the antiviral activity of an antiviral compound being administered to said mammal, which depends on viral-induced enzyme(s) for conversion to a deleterious substrate and/or inhibitor of viral DNA polymerase, and which comprises administering to said mammal an effective potentiating amount of an RR inhibitor of formula (III) (as defined above) or a physiologically acceptable salt thereof.

An advantage of the combination according to the invention is that it enables one to obtain an improved antiviral efficacy. Furthermore, a lower dosage of an antiviral compound (compared with the compound used alone) can be efficacious, thereby improving the therapeutic index of the antiviral compound. Thus, for example, the combination may be used to treat conditions which would otherwise require relatively large dosages of the antiviral compound at which toxicity problems may occur.

The combination according to the invention is especially applicable to the treatment of herpes simplex types 1 and 2 infections and varicella zoster virus infections (e.g., shingles).

DESCRIPTION OF THE PREFERRED EMBODIMENT

With regard to the antiviral compound, this can be selected from any compound that is activated in vivo by virus-induced enzyme(s) as defined above. Such compounds are generally substrates for an appropriate kinase enzyme of viral origin which phosphorylates the compounds to form a monophosphate which, per se or in a metabolically transformed form, is then phosphorylated (by kinase enzymes of either viral or cellular origin) to form the diphosphate and finally the triphosphate DNA polymerase inhibitor or deleterious substrate. The use of an antiviral compound that is selectively phosphorylated by viral enzymes rather than by cellular enzymes provides a greater concentration of the phosphorylated (activated) antiviral compound in infected cells than in non-infected cells. Thus the activated antiviral compound causes selective toxicity to the virus, inhibiting virus replication. It is preferred to use an antiviral compound that is not only a DNA polymerase inhibitor but is also, when incorporated into the viral DNA chain, a chain terminator and, possibly, an apparent inactivator of the viral DNA polymerase.

Thus, for example, acyclovir, as mentioned above, is converted by virus-coded thymidine kinase (but not to any substantial extent by cellular thymidine kinase) to the monophosphate which is then converted to the diphosphate and triphosphate via cellular enzymes. Acyclovir triphosphate is also a DNA chain terminator. The mechanism of acyclovir and other antiviral compounds is described by E. de Clerq in "New Trends in Antiviral Chemotherapy", Archives Internationale de Physiologie et de Biochimie, 87(2), 353–395 (1979) and by P. Furman et al. in "Acyclovir: Mechanism of Action", Human Herpes Infections, edited by C. Lopez and B. Roizman, pp. 129–138, Raven Press, New York (1986).

The antiviral compound employed in the combinations according to the invention may be selected for example from acyclovir and analogs thereof, e.g., those compounds of formula (I)

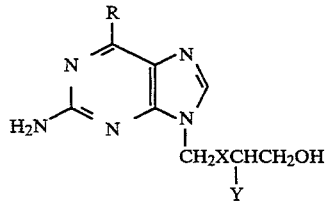

(wherein X is oxygen or sulfur, R is hydrogen, hydroxy or amino and Y is hydrogen or hydroxymethyl) and pharmaceutically acceptable salts and esters thereof.

In addition to acyclovir, examples of preferred compounds of Formula (I) for use in the present invention include:

9-[(2-hydroxy-1-hydroxymethylethoxy)methyl]guanine (see U.S. Pat. No. 4,609,662) as well as prodrugs that are converted in vivo into the above compounds, e.g. 2-amino-9-(2-hydroxyethoxymethyl)adenine and 9-[(2-hydroxy-1-hydroxymethylethoxy)methyl]-2,6-diaminopurine. See U.S. Pat. No. 4,323,573 and G.B. Patent 2,104,070.

Alternatively, the antiviral compound may be 1-[2-hydroxy-1-(hydroxymethyl) ethoxymethyl]cytosine or pharmaceutically acceptable salts and esters thereof. See European Patent Specification 167,385.

Another class of antiviral compounds for use in accordance with the present invention includes compounds of formula (IIA)

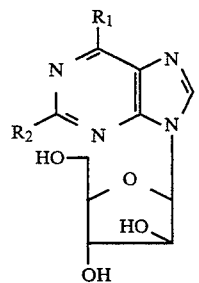

wherein $R^1$ represents a halogen (e.g. chlorine or iodine) atom, a $C_{1-5}$ alkoxy group (e.g. methoxy or ethoxy); halogen-substituted $C_{1-5}$ alkoxy (e.g. trifluoroethoxy); an amino group which is mono- or di-substituted by $C_{1-5}$ alkyl (e.g. methyl or ethyl), $C_{1-5}$ alkyl substituted by one or more fluorine atoms (e.g. 2-fluoroethyl or 2,2,2-trifluoroethyl), or $C_{3-6}$ cycloalkyl (e.g. cyclopropyl); or the amino member of a ring containing 4–7 carbon atoms and optionally a double bond (e.g. piperidino or pyrrolidino) and/or a further nitrogen atom; and $R^2$ represents hydrogen, halogen or amino; and pharmaceutically acceptable salts and esters thereof. See European Patent Specification 294,114.

Preferred compounds of formula (IIA) are 9-β-D-arabinofuranosyl-6-methoxy-9H-purine and 6-methoxy-9-(2-O-valeryl-β-D-arabinofuranosyl)-9H-purine.

Another class of antiviral compounds for use in accordance with the present invention includes compounds of formula (IIB):

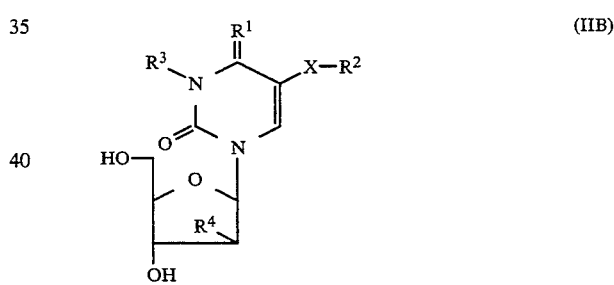

(wherein X represents a vinylene or ethynylene group: $R^1$ represents an oxo or imine group; $R^2$ represents a hydrogen atom, a $C_{1-2}$ alkyl, $C_{3-4}$ branched or cycloalkyl group e.g. isopropyl or cyclopropyl; $R^3$ represents a hydrogen atom or an acyl e.g. $C_{1-4}$ alkanoyl or benzoyl group optionally substituted for example by one or more halogen, alkyl, hydroxy or alkoxy substituents; and $R^4$ represents a hydrogen atom or a hydroxy group; providing that (a) when $R^2$, $R^3$ and $R^4$ each represents a hydrogen atom, $R^1$ does not represent an oxo group and (b) when X represents a vinylene group and $R^2$ represents hydrogen $R^3$ represents and acyl group.

It will be appreciated that when $R^3$ is not an acyl group, the compound of formula (IIB) may exist in its tautomeric form.

The above-mentioned nucleoside analogs also include the pharmaceutically acceptable salts, esters, or salts of such esters, or any other compound which, upon administration to a human subject, is capable of providing (directly or indirectly) the antivirally active metabolite or residue thereof. See European Patent Specification 272,065.

Preferred compounds of formula (IIB) are 1-(β-D-arabinofuranosyl)-5-propynyluracil and 5-propynyl-1-(5-O-pivaloyl-β-D-arabinofuranosyl)uracil.

Examples of preferred RR inhibitors of Formula (III) are those wherein $R^1$ represents hydrogen; and/or $R^2$ represents methyl; and/or $R^3$ represents a group of formula (A) especially those wherein $R^4$, $R^5$ and $R^6$ each represents hydrogen, and/or R7 is phenyl optionally substituted by one or more substituents selected from halogen (e.g. chloro, bromo, iodo, fluoro) $C_{1-6}$ alkyl (e.g. methyl) and $C_{1-6}$ alkoxy (e.g. methoxy).

Examples of particularly preferred ribonucleotide reductase inhibitors include the following novel Compounds and their pharmaceutically acceptable salts.

2-acetylpyridine 5-[(2-methoxy-5-nitroanilino)thiocarbonyl]thiocarbonohydrazone 2-acetylpyridine 5-[(2-pyridylamino)thiocarbonyl]thiocarbonohydrazone 2-acetylpyridine 5-((2,3,4-trichloroanilino)thiocarbonyl)thiocarbonohydrazone 2-acetylpyridine 5-((3-chloro-4-methylanilino)thiocarbonyl)thiocarbonohydrazone 2-acetylpyridine 5-((5-chloro-2-methoxyanilino)thiocarbonyl)thiocarbono hydrazone 2-acetylpyridine 5-((4-chloro-2-methylanilino)thiocarbonyl)thiocarbono hydrazone 2-acetylpyridine 5-((2,3-dichloroanilino)thiocarbonyl)-thiocarbonohydrazone 2-acetylpyridine 5-((2-iodoanilino)thiocarbonyl)thiocaronohydrazone The above compounds are most preferred, especially for use in combination with acyclovir in accordance with the present invention.

The above-defined RR inhibitors of Formula (III), and their pharmaceutically acceptable salts are novel and represent a further feature of the present invention, since they have been found to potentiate, in a synergistic manner, the antiviral effects of the antiviral compounds described above. The RR inhibitors of Formula (III) also have activity against herpes viruses which renders the compounds useful per se in the treatment of herpes virus infections.

According to a further feature of the present invention, we provide the following processes for the preparation of compounds of formula (III) and their pharmaceutical acceptable salts, namely:

(a) A process for the preparation of the above-defined compounds of formula (III), wherein $R^2$ represents a group of formula (A) (as defined herein) which comprises reacting a compound of formula (IV)

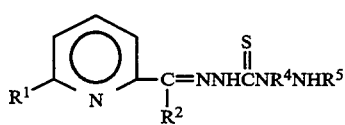

(IV)

(wherein $R^1$, $R^2$, $R^4$ and $R^5$ are as defined in formula (III)) with a compound of formula (V)

    (V)

(wherein X and $R^7$ are defined above in formula (A).

The reaction is advantageously effected in an appropriate solvent medium (e.g. methanol, ethanol, N,N-dimethylacetamide or N,N-dimethylformamide) and a temperature of 0° C. to 80° C.

The compounds of formula (IV) may be synthesised by methods known in the art e.g. as described in International Patent Specification WO8500955 or by methods analogous thereto.

b) A process for the preparation of compounds of formula (III), wherein $R^3$ represents a group of formula (B)(a) (as defined above) in which a compound of Formula (III), wherein $R^3$ represents a group of formula (A) (wherein $R^4$ and $R^5$ are hydrogen) is:
  (i) heated to at least 40° C. (preferably in the range 40° C. to 100° C.), conveniently in an appropriate solvent medium (e.g. methanol or ethanol), or
  (ii) treated under basic conditions e.g. in the presence of a tertiary amine (e.g. triethylamine or diisopropylethylamine) and, if desired, in the presence of an oxidising agent (e.g. hydrogen peroxide or m-chloro perbenzoic acid). The latter base treatment is conveniently effected at a temperature of 0° C. to 100° C.

c) A process for the preparation of a compound of formula (III), wherein $R^3$ represents a group of formula (B)(b) (as defined above) which comprises reacting a compound of formula (IV) wherein $R^4$ and $R^5$ are both hydrogen (as defined above) with a compound of formula (VI)

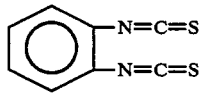

(VI)

(wherein X is as previously defined).

The reaction is conveniently effected at a temperature of 0° C. to 80° C., in an appropriate solvent (e.g. methanol, ethanol, N,N-dimethyformamide or N,N-dimethyl acetamide).

d) A process for the preparation of compounds of formula (III) wherein $R^3$ represents a group of formula (B)(c) (as defined above) which comprises either:
  i) reacting a compound of formula (III), wherein $R^3$ represents a group of formula (A) with a strong acid (e.g. trifluoroacetic acid); or
  ii) reacting a compound of formula (IV) (as defined herein) with carbon disulphide, conveniently in an appropriate solvent (e.g. methanol, ethanol, water or mixtures thereof) and an appropriate base (e.g. sodium hydroxide, potassium hydroxide, sodium methoxide, or potassium methoxide); to form a Compound of formula (B)(c) wherein $R^{11}$ represents hydrogen and, if desired, reacting the resulting compound with a $C_{1-6}$ alkylating agent (e.g. methyl iodide) to form a corresponding compound of formula (B)(c) wherein $R^{11}$ represents $C_{1-6}$ alkyl. The alkylation reaction is advantageously effected in arm appropriate solvent (e.g. methanol, ethanol, water or mixtures thereof) and in the presence of an appropriate base (e.g. sodium hydroxide, potassium hydroxide, sodium methoxide or potassium methoxide).

Salts of the RR inhibitors, according to the invention, which may be conveniently used in therapy, include pharmaceutically acceptable base salts, derived from an appropriate base, such as alkali metal (e.g. sodium), alkaline earth metal (e.g. magnesium) salts, ammonium and NX+4 (wherein X is $C_{1-4}$ alkyl) salts. Suitable pharmaceutically acceptable salts also include, but are not limited to, those prepared from the following acids: hydrochloric, hydrobromic, sulfuric, nitric, phosphoric, maleic, salicylic, p-toluene-sulfonic, tartaric, citric, acetic, methanesulfonic, formic, succinic, naphthalene-2-sulfonic, isethionic, lactobionic and benzenesulfonic. The pharmaceutically acceptable salts of the above RR inhibitors may be prepared in conventional manner for example by treatment with the appropriate base or acid.

The combinations according to the invention may be administered to the subject concerned in conventional manner. As indicated above, the antiviral compound and the RR inhibitor may be administered simultaneously (e.g. in a unitary pharmaceutical formulation) or separately (e.g. in separate pharmaceutical formulations). In general, the combinations may be administered by the topical, oral, rectal or parenteral (e.g. intravenous, subcutaneous or intramuscular) route. The dosage of the combination will depend on the condition being treated, the particular antiviral compound and RR inhibitor concerned, and other clinical factors such as the weight and condition of the patient and the routes of administration of the compounds. However, for administration by the oral route, a dosage of the antiviral compound of 1 to 150 mg/kg/day, more preferably 5-125 mg/kg/day, and most preferably 15 to 80 mg/kg/day, is generally sufficient. The amount of RR inhibitor in the combination will be determined from the amount of antiviral compound specified above and the desired ratio of antiviral compound to RR inhibitor.

The ratio of antiviral compound to RR inhibitor is preferably in the range of about 0.5:1 to 50:1 (w/w), more preferably 1:1 to 30:1 (w/w), and most preferably 5:3 (w/w).

For convenience, the antiviral compound and RR inhibitor are preferably administered in a unitary pharmaceutical formulation. Thus, the present invention further provides a pharmaceutical formulation comprising a combination according to the invention, together with at least one pharmaceutical carrier or excipient, the antiviral compound and RR inhibitor being present in the formulation in a ratio whereby a synergistic antiviral effect is achieved.

Formulations include those suitable for oral, rectal, nasal, topical (including buccal and sublingual), vaginal, parenteral (including subcutaneous, intramuscular, intravenous, intradermal, intrathecal and epidural) administration. The formulation may conveniently be presented in unit dosage form and may be prepared by conventional pharmaceutical techniques. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may additionally contain other adjunct components conventionally found in pharmaceutical compositions, at their art-established usage levels. Thus, for example, the compositions may contain additional compatible pharmaceutically-active materials which enhance antiviral effectiveness or facilitate combination therapy (such as potentiating agents, antivirals, antimicrobials, antipruritics, astringents, local anesthetics or anti-inflammatory agents), or may contain materials useful in physically formulating various dosage forms of the composition of present invention, such as excipients, dyes, perfumes, fragrances, preservatives, antioxidants, opacifiers, thickening agents and stabilizers. These materials, when added, should not unduly interfere with the penetration enhancement of the compositions of this invention. Such formula modifications to improve cosmetic acceptability are well within the skill of workers in the cosmetic and dermatological arts and, by themselves, constitute no part of the present invention.

Formulations of the present invention suitable for oral administration may be presented as discrete units such as capsules, cachets or tablets each containing predetermined mounts of the active ingredients; as powders or granules; as solutions or suspensions in an aqueous liquid or a non-aqueous liquid; or as oil-in-water emulsions or water-in-oil liquid emulsions. A tablet may be made by compression or molding, optionally with one or more accessory ingredients. Compressed tablets may be prepared by compressing in a suitable machine, the active ingredients in a free-flowing form such as a powder or granules, optionally mixed with a binder, lubricant, inert diluent, preservative, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredients therein.

For infections of the eye or other external tissues, e.g., mouth and skin, the formulations are preferably applied as a topical ointment or cream containing the combined active ingredients in a total amount of, for example, 0.075 to 30% w/w, preferably 0.2 to 20% w/w and most preferably 0.4 to 15% w/w. When formulated in an ointment, the active ingredients may be employed with either paraffinic or a water-miscible ointment base. Alternatively, the active ingredients may be formulated in a cream with an oil-in-water cream base.

If desired, the aqueous phase of the cream base may include, for example at least 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs.

The oily phase of the emulsions of this invention may be constituted from known ingredients in a known manner. While the phase may comprise merely an emulsifier, it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations.

Emulsifiers and emulsion stabilizers suitable for use in the formulation of the present invention include Tween 60, Span 80, cetostearyl alcohol, myristyl alcohol, glyceryl monostearate, sodium lauryl sulfate, Myrj and Birj.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The antiviral active ingredients are preferably present in such formulations in a concentration of 0.5 to 20%, advantageously 0.5 to 10% and particularly about 1.5% w/w.

Formulations suitable for topical administration in the mouth include lozenges comprising the active ingredient in a flavored basis, usually sucrose and acacia or tragacanth; pastilles comprising the active ingredient in an inert bases such as gelatin and glycerin, or sucrose and acacia; and mouth washes comprising the active ingredients in a suitable liquid carrier. Formulations for rectal administration may be presented as a suppository with a suitable base comprising for example cocoa butter or a salicylate.

Formulations suitable for nasal administration wherein the carrier is a solid include a coarse powder having a particle size for example in the range 20 to 500 microns which is administered in a manner in which snuff is taken, i.e., by rapid inhalation through the nasal passage from a container of the powder held close up to the nose. Suitable formulations wherein the carrier is a liquid, for administration as for example a nasal spray or as nasal drops, include aqueous or oil solutions of the active ingredients.

Formulations suitable for vaginal administration may be presented as pessaries, tampons, creams, gels, pastes, foams or spray formulations containing in addition to the active ingredients such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient. Suitable formulations also include aqueous and non-aqueous sterile suspensions which may contain suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solution and suspensions may be prepared from sterile powders, granules and tablets of the kind previously described.

Preferred unit dosage formulations are those containing a daily dose or unit, daily sub-dose, or an appropriate fraction thereof, of the active ingredients.

It should be understood that in addition to the ingredients particularly mentioned above, the formulations of this invention may include other agents conventional in the art having regard to the type of formulation in question, for example, those suitable for oral administration may include flavoring agents.

Antiviral Activity

The ribonucleotide reductase inhibitors of the present invention were shown by use of the dye uptake method described by McLaren, Ellis and Hunter in Antivir. Res. 3, 223–234 (1983) to potentiate the in vitro antiviral effects of acyclovir. Vero cells (20,000 cells/well) were incubated in microtiter wells for 24 hours. Various concentrations of acyclovir and the ribonucleotide reductase inhibitors were added and the cells were infected with 30 infectious particles/well of HSV-1 or HSV-2. After 3 days incubation, the antiviral effects were assessed by determining the prevention of the cytopathic effects of the viruses. Examples of the synergistic antiherpes activity of 2-acetylpyridine (4,5-dihydro-5-thioxo-1,3,4-thiadiazol-2-yl)-hydrazone (Compound A) and acyclovir (ACV) are given below.

An example of the synergistic antiherpes activities of Compound A and ACV:

| | $IC_{50}$[a] | | |
| Compound(s) | Observed | Calculated[b] | Fold potentiated[c] |
|---|---|---|---|
| ACV | 5.77 | 5.7 | — |
| ACV plus 0.4 μM Compound A (0%)[d] | 2.9 | 5.7 | 2.0 |
| ACV plus 0.9 μM Compound A (0%)[d] | 0.87 | 5.7 | 6.6 |
| ACV plus 1.3 μM Compound A (21%)[d] | 0.32 | 5.2 | 16 |

[a] Concentration (μM) of ACV required to inhibit HSC-2 replication by 50%.
[b] Theoretical value for the additive combined effects of ACV and Compound A.
[c] Ratio of calculated $IC_{50}$ to observed $IC_{50}$.
[d] Parenthetical number is the % inhibition of virus replication by Compound A alone, which had an $IC_{50}$ of 1.6 μM.

2. The inhibitory effects of compounds of this invention on the replication of varicella-zoster virus (Oka strain) are assessed by an ELISA procedure (Berkowitz, F. E., and Levin, M. J. (1985). Antimicrob. Agents and Chemother. 28:207–210) that is modified as follows. Infections are initiated in the presence of drug, rather than before drug addition. At the end of the three day incubation of drug and virus with uninfected cells (human melanoma, strain M36)., the 96-well plates are centrifuged for 5 minutes at 200×g to sediment detached cells prior to glutaraldehyde fixation. The present ELISA uses an alkaline phosphatase-conjugated anti-human IgG as the second antibody. The rate of cleavage of p-nitrophenyl phosphate by bound alkaline phosphatase is determined as described elsewhere (Tadepalli, S. M., Quinn, R. P., and Averett, D. R. 1986. Antimicrob. Agents and Chemother. 29:93–98). Uninfected cells are used to obtain the blank reaction rates, which are subtracted from the rates obtained with the virus present. This assay is suitable to detect progeny virus in cultures that were initially infected with 15 to 3600 infectious particles per well.

The following Examples are provided by way of illustration of the present invention and should in no way be construed as limitation thereof.

EXAMPLES
RR Inhibitors

Preparation 1: 2-Acetylpyridine thiocarbonohydrazone

To a solution of distilled 2-acetylpyridine (Aldrich Chemical Co., Milwaukee, Wis. 53233), 33.3 g, in 300 mL of methanol was added thiocarbohydrazide (Sigma Chemical Co., St. Louis, Mo., 63178), 29.18 g. The resulting mixture was hearted at reflux, under nitrogen, overnight. A precipitate was collected by filtration, washed with cold methanol, and dried to give 56.0 g (97%) of 2-acetylpyridine thiocarbonohydrazone as a white crystalline solid, m.p. 185°–186° C. (dec.).

$^1$H-NMR: (DMSO-$d_6$) δ 2.34 (s, 3H, $CH_3$), 5.00 (br s, 2H, $NH_2$), 7.36 (ddd; 1H; J=1.0, 4.9, 7.5; aromatic CH), 7.77 (dr; 1H; J=1.7, 7.8; aromatic CH), 8.53 (m, 2H, aromatic CH), 9.96 (br s, 1H, NH), 10.31 (s, 1H, NH).

The following compounds (preparations 2–3) were prepared using the general method described in preparation 1:

Preparation 2: 2-Formylpyridine thiocarbonohydrazone

Reaction of 2-pyridinecarboxaldehyde (Aldrich), 10.13 g, and thiocarbohydrazide (Sigma), 10.04 g, in 250 mL of methanol gave 18.2 g (92%) of 2-formylpyridine thiocarbonohydrazone as a white crystalline solid, m.p. 162°–164° C. (dec.).

$^1$H-NMR: (DMSO-$d_6$) δ 4.89 (br s, 2H, NH) 7.33 (m, 1H aromatic CH), 7.79 (dr, 1H, J=1.7, 7.5, aromatic CH), 8.02 (s, 1H, aromatic CH), 8.35 (d, 1H, J=8, aromatic CH), 8.52 (dd, 1H, J=1, 4.1, aromatic CH), 10.16 (br s, 1H, CHO), 11.62 (br s, 1H, NH).

Preparation 3: 2-Formyl-6-methylpyridine thiocarbonohydrazone

Reaction of 6-methyl-2-pyridinecarboxaldehyde (Aldrich), 10.29 g, and thiocarbohydrazide (Sigma), 9.02 g, gave 17.4 g (89%) of 2-formyl-6-methylpyridine thiocarbonohydrazone as a light yellow crystalline solid, m.p. 166°–168° C. (dec.).

$^1$H-NMR: (DMSO-$d_6$) δ 2.44 (s, 3H, $CH_3$), 4.88 (br s, 2H, NH), 7.19 (d, 1H, J=7.6, aromatic CH), 7.67 (t, 1H, J=7.6, aromatic CH), 7.97 (s, 1H, aromatic CH), 8.15 (d, 1H, J=7.8, aromatic CH), 9.98 (br s, 1H, CHO), 11.60 (br s, 1H, NH).

Preparation 4: 2-Acetylpyridine 5-[(methylamino) thiocarbonyl]thiocarbonohydrazone A 1 L 3-neck flask fitted with an overhead mechanical stirrer, condenser, glass stopper, and a nitrogen line was charged with 2-acetylpyridine thiocarbonohydrazone, 5.37 g, and 500 mL of absolute ethanol. The resulting mixture was heated at reflux for 5 min to dissolve most of the solid material. The mixture was allowed to cool below reflux temperature and methyl isothiocyanate (Aldrich), 2.20 mL (2.35 g), was added. The reaction mixture was heated at reflux for 30 min, allowed to cool to RT, and subsequently cooled in an ice-water bath. A precipitate was collected by filtration, washed with cold ethanol, and dried in vacuo to give 6.74 g (93.3%) of 2-acetylpyridine 5-[(methylamino)thiocarbonyl]thiocarbonohydrazone as a white crystalline solid, m.p. 178.0°–178.5° C. (dec.).

$^1$H-NM: (DMSO-$d_6$) δ2.39 (s, 3H, $COCH_3$), 2.86 (d, 3H, J=4, $NCH_3$), 7.38 (m, 1H, aromatic. CH), 7.85 (m, 1H, NH), 8.56 (m, 2H, aromatic CH), 9.43 (br s, 1H, NH), 10.32 (br s, 1H, NH), 10.82 (br s, 1H, NH).

The following compounds (Examples 1–11) were prepared using the general method described in Preparation 4:

Novel RR Inhibitors

Example 1

2-Acetylpyridine 5-[[(morpholinoethyl)amino]thiocarbonyl]thiocarbonohydrazone

Reaction of 2-acetylpyridine thiocarbonohydrazone, 5.26 g, and 2-morpholinoethyl isothiocyanate (Fairfield Chemical Co., Inc., Blythewood, S.C., 29016), 5.05 g, for 1.5 h gave 6.61 g (69.0%) of the title compound as an off-white powder, m.p.161°–162° C. (dec.).

$^1$H-NMR: (DMSO-$d_6$) δ2.40 (m, 12H), 3.34 (br s, 4H), 7.39 (m, 1H, aromatic CH), 7.78 (t, 1H, J=8, aromatic CH), 8.57 (m, 2H, aromatic CH), 9.53 (br s, 1H, NH), 10.88 (br s, 1H, NH).

Example 2

2-Acetylpyridine 5[(benzylamino)thiocarbonyl]thiocarbonohydrazone

Reaction of 2-acetylpyridine thiocarbonohydrazone, 5.02 g, and benzyl isothiocyanate (Aldrich), 3.80 mL (4.27 g), gave 8.17 g (95%) of the title compound as a white crystalline solid, m.p. 202°–204° C. (dec.).

$^1$H-NMR: (DMSO-$d_6$) δ2.39 (s, 3H, $CH_3$), 4.72 (d, 2H, J=6, $CH_2$), 7.30 (m, 6H, aromatic CH), 7.79 (dt; 1H; J=1.5, 7.5; aromatic CH), 8.46 (m, 1H, NH), 8.56 (m, 2H, aromatic CH), 9.56 (br s, 1H, NH), 10.39 (br s, 1H, NH), 10.89 (br s, 1H, NH).

Example 3 2-Acetylpyridine 5-(anilinothiocarbonyl)thiocarbonohydrazone

Reaction of 2-acetylpyridine thiocarbonohydrazone, 5.12 g, and distilled phenyl isothiocyanate (Aldrich), 3.10 mL (3.50 g), gave 7.33 g (87%) of the title compound as a white solid, m.p. 178°–180° C. (dec.).

$^1$H-NMR: (DMSO-$d_6$) δ2.42 (s, 3H, $CH_3$), 7.12 (t, 1H, J=7, aromatic CH), 7.27–7.53 (m, 5H, aromatic CH), 7.81 (dt; 1H; J=1, 7; aromatic CH), 8.58 (dd; 2H; J=1, 4; aromatic CH), 9.65 (br s, 1H, NH), 9.82 (br s, 1H, NH), 10.50 (br s, 1H, NH), 10.95 (br s, 1H, NH).

Example 4

2-Acetylpyridine 5-[((3-morpholinopropyl)amino)thiocarbonyl]-thiocarbonohydrazone Reaction of 2-acetylpyridine thiocarbonohydrazone, 7.30 g, and 3-morpholinopropyl isothiocyanate (Fairfield), 7.80 g, in 700 mL of absolute ethanol gave 11.75 g (85%) of the title compound as a white solid, m.p. 195°–197° C. (dec.).

$^1$H-NMR: (DMSO-$d_6$) δ1.66 (pentet, 2H, J=6.5, $CCH_2C$), 2.32 (br s, 6H, $CH_2$), 2.39 (s, 3H, $CH_3$), 3.50 (m, 6H, $CH_2$), 7.38 (m, 1H, aromatic CH), 7.78 (dt; 1H; J=2, 8; aromatic CH), 7.92 (br s, 1H, NH), 8.57 (m, 2H, aromatic CH), 9.40 (br s, 1H, NH), 10.30 (br s, 1H, NH), 10.82 (br s, 1H, NH).

Example 5

2-Acetylpyridine 5-[(2-(methoxyanilino)thiocarbonyl]thiocarbonohydrazone

Reaction of 2-acetylpyridine thiocarbonohydrazone, 5.03 g, and 2-methoxyphenyl isothiocyanate (Aldrich), 3.50 mL (4.19 g), for 2 h gave 3.63 g of a yellow powder. The powder was dissolved in 200 mL of DMF, filtered, and to the filtrate was added 150 mL of $H_2O$, giving a white precipitate which was removed by filtration. The filtrate was concentrated in vacuo to a volume of approximately 100 mL and allowed to stand overnight. A precipitate was collected by filtration to give 2.59 g (29%) of the title compound as a yellow powder, m.p. 146°–148° C. (dec., turned bright red and evolved $H_2S$ to re-solidify and at 180°–182° C. decomposed again to give a dark red melt).

$^1$H-NMR: (DMSO-$d_6$) δ2.43 (s, 3H, CCH$_3$), 2.72 and 2.88 (s, DMF), 3.85 (br s, sharp s at 80° C. 3H OCH$_3$) 6 92 (m, 2H, aromatic CH), 7.06 (m, 2H. aromatic CH), 7.40 (m, 1H, aromatic CH), 7.82 (t, 1H, J=7.5, aromatic CH), 7.94 (s, DMF), 8.18 (m, 1H, aromatic CH), 8.52 (br s, 1H, NH), 8.59 (d, 1H, J=5, aromatic CH), 9.20 (brs, 1H, NH), 10.05 (br s, 1H, NH), 11.01 (br s, 1H, NH).

Example 6

2-Acetylpyridine 5-[(3-trifluoromethylanilino)thiocarbonyl]thiocarbonohydrazone Reaction of 2-acetylpyridine thiocarbonohydrazone, 5.02 g, and 3-trifluoromethylphenyl isothiocyanate (Trans World Chemicals, Inc., Chevy Chase, Md., 20815), 5.85 g, gave 6.03 g (61%) of the title compound as a white powder, m.p. 181°–184° C. (dec., turned bright red and evolved $H_2S$ to re-solidify and at 195°–197° C. decomposed again to give a dark red melt).

$^1$H-NMR: (DMSO-$d_6$) δ2.42 (s, 3H, CH$_3$), 7.35–7.58 (m, 3H, aromatic CH), 7.83 (m, 3H, aromatic CH), 8.57 (d, 2H, J=5, aromatic CH), 9.88 (br s, 1H, NH), 10.03 (br s, 1H, NH), 10.45 (br s, 1H, NH), 10.99 (br s, 1H, NH).

Example 7

2-Acetylpyridine 5-[(4-(dimethylamino)anilino)thiocarbonyl]thiocarbonohydrazone Reaction of 2-acetylpyridine thiocarbonohydrazone, 4.00 g, and 4-(dimethylamino)phenyl isothiocyanate (Trans World), 3.60 g, in 400 mL of absolute ethanol for 45 min gave 5.52 g (75%) of the title compound as a yellow-green powder, m.p. 179.7°–180.5° C. (dec.).

$^1$H-NMR: (DMSO-$d_6$) δ2.39 (s, 3H, CH$_3$), 2.85 (s, 6H, N(CH$_3$)2), 6.65 (d, 2H, J=8.7, aromatic CH), 7.19 (d, 2H, J=8.7, aromatic CH), 7.38 (m, 1H, aromatic CH), 7.80 (dt, 1H, J=1.5, 7.5, aromatic CH), 8.55 (m, 2H, aromatic CH), 9.48 (br s, 1H, NH), 9.62 (br s, 1H, NH), 10.45 (br s, 1H, NH), 10.90 ( s, 1H, NH).

Example 8

2-Acetylpyridine 5-[(3-methoxyanilino)thiocarbonyl]thiocarbonohydrazone

Reaction of 2-acetylpyridine thiocarbonohydrazpne, 4.45 g, and 3-methoxyphenyl isothiocyanate (Trans World), 3.70 g, for 20 min gave 6.88 g (86%) of the title compound as a white solid, m.p. 172°–176° C. (dec., turned bright red and evolved $H_2S$ to re-solidify and at 184° C. decomposed again to give a dark red melt).

$^1$H-NMR: (DMSO-$d_6$) δ2.42 (s, 3H, CCH$_3$), 3.72 (s, 3H, OCH$_3$), 6.70 (m, 1H, aromatic CH), 7.06 (m, 1H, aromatic CH), 7.19 (t, 2H, J=7, aromatic CH), 7.39 (m, 1H, aromatic CH), 7.83 (dr, 1H, J=1, 7, aromatic CH), 8.57 (m, 2H, aromatic CH), 9.60 (br s, 1H, NH), 9.84 (br s, 1H, NH), 10.47 (br s, 1H, NH), 10.97 (br s, 1H, NH).

Example 9

N-[[5-[1-(2-Pyridyl)ethylidene]thiocarbonohydrazido]-thiocarbonyl]benzamide

Reaction of 2-acetylpyridine thiocarbonohydrazone, 5.76 g, and benzoyl isothiocyanate (Aldrich), 5.61 g, for 20 min gave 9.73 g (95%) of the title compound as a white powder, m.p. 195°–196° C. (dec.).

$^1$H-NMR: (DMSO-$d_6$) δ2.44 (s, 3H, CH$_3$), 7.40–8.64 (m, 9H, aromatic CH), 1.29 (br s, 1H, NH), 11.50 (br s, 1H, NH), 12.00 (s, 1H, NH).

Example 10

2-Acetylpyridine 5-[(2-methoxy-5-nitroanilino)thiocarbonyl]thiocarbonohydrazone Reaction of 2-acetylpyridine thiocarbonohydrazone, 5.28 g, and 2-methoxy-5-nitrophenyl isothiocyanate (Trans World), 5.70 g, gave 8.48 g (80%) of the title compound as a yellow powder, m.p. 212°–213° C. (dec.).

$^1$H-NMR: (DMSO-$d_6$) δ2.43 (s, 3H, CCH$_3$), 3.90 (s, 3H, OCH$_3$), 7.26 (m, 1H, aromatic CH), 7.40 (m, 1H, aromatic CH), 7.83 (dr, 1H, J=1.5, 7.5, aromatic CH), 8.06 (dd, 1H, J=3, 9, aromatic CH), 8.45 (br s, 1H, aromatic CH), 8.58 (dd, 1H, J=1, 4, aromatic CH), 9.10 (br s, 1H, aromatic CH), 9.40 (br s, 1H, NH), 10.22 (br s, 1H, NH), 10.85 (br s, 1H, NH), 11.03 (br s, 1H, NH).

Example 11

2-Acetylpyridine 5-[(4-nitroanilino)thiocarbonyl]thiocarbonohydrazone and 2-Acetylpyridine [5-(4-nitroanilino)-1,3,4-thiadiazol-2-yl]hydrazone Reaction of 2-acetylpyridine thiocarbonohydrazone, 5.05 g, and 4-nitrophenyl isothiocyanate (Trans World), 5.20 g, gave 6.72 g of a red solid. The material was suspended in 3 L of methanol and stirred at 40° C. for 2 h. The undissolved red solid was collected by filtration (the filtrate was treated as indicated below), taken up in 175 mL of DMF and filtered hot. Addition of 50 mL of $H_2O$ caused precipitation of a red solid which was collected by filtration, washed with $H_2O$, ethanol, and ether, and dried to give 0.95 g (11%) of 2-acetylpyridine [5-(4-nitroanilino)-1,3,4-thiadiaza-2-yl]hydrazone as an orange-red powder, m.p. >260° C.

$^1$H-NMR: (DMSO-$d_6$) δ2.37 (s, 3H, CH$_3$), 7.37 (m 1H, aromatic CH), 7.72 (d, 2H, J=9, aromatic CH), 7.83 (m, 1H, aromatic CH), 7.92 (m, 1H, aromatic CH), 8.23 (d, 2H, J=9, aromatic CH), 8.58 (m, 1H, aromatic CH), 10.71 (br s,. 1H, NH), 11.65 (br s, 1H, NH).

The filtrate (indicated above) was concentrated in vacuo to a volume of approximately 800 mL, cooled, and the resulting precipitate was collected by filtration, washed with cold methanol, and dried to give 1.59 g (17%) of 2-acetylpyridine 5-[(nitroanilino)thiocarbonyl]thiocarbonohydrazone as a tan powder, m.p. 230° C. (dec.).

$^1$H-NMR: (DMSO-d6) δ2.49 (s, 3H, CH$_3$), 7.36–8.62 (m, 8H, aromatic CH), 10.05 (br s, 1H, NH), 10.25 (br s, 1H, NH), 10.55 (br s, 1H, NH), 11.06 (br s, 1H, NH).

Example 12

2-Acetylpyridine 5-[(4-chloroanilino)thiocarbonyl]thiocarbonohydrazone

To a solution of 2-acetylpyridine thiocarbonohydrazone, 5.52 g, in 195 mL of dry DMF was added 4-chlorophenyl isothiocyanate (Trans World), 4.48 g, and the resulting mixture was stirred at RT for 30 min. The solution was cooled in an ice bath and H$_2$O was added. A precipitate was collected, washed with H$_2$O, and dried in vacuo to give 9.1 g (91%) of 2-acetylpyridine 5-[(4-chloroanilino) thiocarbonyl]thiocarbonohydrazone as a white powder, m.p. 181°–182° C. (dec.).

$^1$H-NMR: (DMSO-d$_6$) δ2.41 (s, 3H, CH$_3$); 7.33–8.58 (m, 8H, aromatic CH), 9.75 (br s, 1H, NH), 9.87 (br s, 1H, NH), 10.43 (br s, 1H, NH), 10.96 (s, 1H, NH).

The following compounds (examples 13–29) were prepared using the general method described in example 12:

Example 13

2-Acetylpyridine 5-[(3-chloroanilino)thiocarbonyl]thiocarbonohydrazone

Reaction of 2-acetylpyridine thiocarbonohydrazone, 7.00 g, and 3-chlorophenyl isothiocyanate (Trans World), 5.69 g, in 245 mL of dry DMF gave 12.71 g (100%) of the title compound as an orange powder, m.p. 168°–171° C. (dec.).

$^1$H-NMR: (DMSO-d$_6$) δ2.41 (s, 3H, CH$_3$); 7.15–7.85 (m, 7H, NH, aromatic CH), 8.57 (d, 2H, J=4, aromatic CH), 9.77 (br s, 1H, NH), 10.01 (br s, 1H, NH), 10.42 (br s, 1H, NH).

Example 14

2-Acetylpyridine 5-[(2-chloroanilino)thiocarbonyl]thiocarbonohydrazone

Reaction of 2-acetylpyridine thiocarbonohydrazone, 7.00 g, and 2-chlorophenyl isothiocyanate (Trans World), 5.67 g, in 245 mL of dry DMF gave 8.74 g of a tan powder. Recrystallization from DMF/H$_2$O afforded 5.69 g (45%) of the title compound as a light yellow powder, m.p. 159°–160° C. (dec.).

$^1$H-NMR: (DMSO-d$_6$) δ2.48 (s, 3H, CH$_3$), 7.17–8.58 (m, 8H, aromatic CH), 9.39 (br s, 1H, NH), 9.95 (br s, 1H, NH), 10.52 (br s, 1H, NH), 10.96 (s, 1H, NH).

Example 15

2-Acetylpyridine 5-[(2-bromoanilino)thiocarbonyl]thiocarbonohydrazone

Reaction of 2-acetylpyridine thiocarbonohydrazone, 7.00 g, and 2-bromophenyl isothiocyanate (Trans World), 7.15 g, in 245 mL of dry DMF for 2 h gave 19.18 g of an orange powder. Recrystallization from DMF/H$_2$O afforded 12.33 g (87%) of 2-acetylpyridine 5-[(2-bromoanilino)thiocarbonyl]thiocarbonohydrazone as a light yellow powder, m.p. 155°–158° C. (dec.).

$^1$H-NMR: (DMSO-d$_6$) F101 δ2.41 (s, 3H, CH$_3$), 7.10–7.85 (m, 7H, NH, aromatic CH), 8.57 (d, 2H, J=4, aromatic CH), 9.36 (br s, 1H, NH), 9.95 (br s, 1H, NH), 10.52 (br s, 1H, NH).

Example 16

3-[1-[[[1-(2-Pyridyl)ethylidene]hydrazino]thiocarbonyl]-4-thiosemicarbazido]benzonitrile Reaction of 2-acetylpyridine thiocarbonohydrazone, 6.00 g, and 3-cyanophenyl isothiocyanate (Trans World), 4.59 g, in 210 mL of dry DMF for 15 min to give 9.93 g (94%) of the title compound as an off-white powder, m.p. 178°–180° C. (dec.).

$^1$H-NMR: (DMSO-d$_6$) δ2.42 (s, 3H, CH$_3$), 7.36–8.59 (m, 8H, aromatic CH), 9.87 (br s, 1H, NH), 10.08 (br s, 1H, NH), 10.50 (br s, 1H, NH), 11.01 (s, 1H, NH).

Example 17

4[1-[[[1-(2-pyridyl)ethylidene]hydrazino]thiocarbonyl]-4-thiosemicarbazido]benzonitrile Reaction of 2-acetylpyridine thiocarbonohydrazone, 4.80 g, and 4-cyanophenyl isothiocyanate (Trans World), 3.67 g, in 170 mL of dry DMF gave 8.5 g (100%) of the title compound as a yellow powder, m.p. 241°–242° C. (dec.).

$^1$H-NMR: (DMSO-d$_6$) δ2.42 (s, 3H, CH$_3$), 7.38 (dr, 1H, J=6.5, 6.5, aromatic CH), 7.28–8.59 (m, 7H, aromatic CH), 9.90 (br s, 1H, NH), 10.12 (br s, 1H, NH), 10.50 (s, 1H, NH); 11.01 (s, 1H, NH).

Example 18

3-[1-[[[1-(2-Pyridyl)ethylidene]hydrazino]thiocarbonyl]-4-thiosemicarbazido]benzoic acid Reaction of 2-acetylpyridine thiocarbonohydrazone, 8.70 g, and 3-carboxyphenyl isothiocyanate (Trans World), 7.44 g, in 300 mL of dry DMF overnight gave 13.42 g (83%) of the title compound as a white powder, m.p. 183°–185° C. (dec.).

$^1$H-NMR: (DMSO-d$_6$) δ 2.42 (s, 3H, CH$_3$), 7.35–8.58 (m, 8H, aromatic CH), 9.81 (br s, 1H, NH), 9.92 (br s, 1H, NH), 10.48 (br s, 1H, NH), 10.95 (s, 1H, NH), 12.91 (br s, 1H, COOH).

Example 19

4-[1-[[[1-(2-Pyridyl)ethylidene]hydrazino]thiocarbonyl]-4-thiosemicarbazido]benzoic acid Reaction of 2-acetylpyridine thiocarbonohydrazone, 4.41 g, and 4-carboxyphenyl isothiocyanate (Trans World), 3.78 g, in 150 mL of dry DMF gave 6.39 g of an off-white powder. Recrystallization from DMF/H$_2$O afforded 4.99 g (54%) of the title compound as an off-white powder, m.p. 269°–270° C. (dec.).

$^1$H-NMR: (DMSO-d$_6$) δ2.42 (s, 3H, CH$_3$), 2.72 and 2.87 (s, DMF), 7.35–8.59 (m, 8H, aromatic CH), 9.80 (br s, 1H, NH), 10.00 (br s, 1H, NH), 10.50 (br s, 1H, NH), 10.96 (s, 1H, NH), 12.71 (br s, 1H, COOH).

Example 20

2-Acetylpyridine 5-[[(1-adamantyl)amino]thiocarbonyl]thiocarbonohydrazone

Reaction of 2-acetylpyridine thiocarbonohydrazone, 5.21 g, and 1-adamantyl isothiocyanate (Aldrich), 5.00 g, in 200 mL of dry DMF overnight gave, after recrystallization from acetone, 1.20 g (11%) of the title compound as off-white crystals, m.p. 172°–177° C. (dec.).

¹H-NMR: (DMSO-d₆) δ1.61 (br s, 6H, CH₂), 2.03 (br s, 3H, CH), 2.07 (s, acetone), 2.16 (br s, 6H, CH₂), 2.40 (s, 3H, CH₃), 7.38 (m, 1H, aromatic CH), 7.81 (dt, 1H, J=2, 8, aromatic CH), 8.39 (m, 1H, aromatic CH), 8.57 (m, 1H, aromatic CH), 10.65 (br s, 1H, NH), 10.89 (br s, 1H, NH).

Example 21

2-Acetylpyridine 5-[[[2-(2-pyridyl)ethyl]amino]thiocarbonyl]thiocarbonohydrazone Reaction of 2-acetylpyridine thiocarbonohydrazone, 5.60 g, and b-2-pyridylethyl isothiocyanate (Trans World), 4.39 g, in 196 mL of dry DMF overnight gave 8.70 g (87%) of the title compound as a pale yellow powder, m.p. 179°–181° C. (dec.).

¹H-NMR: (DMSO-d₆) δ2.41 (s, 3H, CH₃), 2.97 (t, 2H, J=7, CH₂), 3.76 (m, 2H, CH₂), 7.14 (dr, 1H, J=6, aromatic CH), 7.27 (d, 1H, J=7.7, aromatic CH), 7.38 (dt, 1H, J=5, 6, aromatic CH), 7.65 (dr, 1H, J=7.6, aromatic CH), 7.78 (dt, 1H, J=7.5, 8, aromatic CH), 8.16 (br t, 1H, NH), 8.38 (d, 1H, J=4, aromatic CH), 8.55 (m, 2H, aromatic CH), 9.50 (br s, 1H, NH), 10.36 (br s, 1H, NH), 10.86 (s, 1H, NH).

Example 22

2-Acetylpyridine 5-[(cyclopentylamino)thiocarbonyl]thiocarbonohydrazone

Reaction of 2-acetylpyridine thiocarbonohydrazone, 6.00 g, and cyclopentyl isothiocyanate (Trans World), 3.64 g, in 210 mL of dry DMF overnight gave 8.02 g (83%) of the title as a light yellow powder, m.p. 180°–182° C. (dec.).

¹H-NMR: (DMSO-d₆) δ1.46–1.88 (m, 8H, CH₂), 2.40 (s, 3H, CH₃), 4.53 (br m, 1H, CH), 7.38 ( dt, 1H, J=4.8, 4.8, aromatic CH), 7.76 (br s, 1H, NH), 7.82 (dt, 1H, J=7.5, 8, aromatic CH), 8.52 (d, 1H, J=8, aromatic CH), 8.58 (d, 1H, J=4.8, aromatic CH), 9.38 (br s, 1H, NH), 10.36 (br s, 1H, NH), 10.83 (s, 1H, NH).

Example 23

Ethyl[[5-[1(2-pyridyl)ethylidene]thiocarbonohydrazido]thiocarbonyl]carbamate

Reaction of 2-acetylpyridine thiocarbonohydrazone, 6.60 g, and ethoxycarbonyl isothiocyanate (Trans World), 4.13 g, in 230 mL of dry DMF gave 7.60 g (71%) of the title compound as a white powder, m.p. 195°–197° C. (dec.).

¹H-NMR: (DMSO-d₆) δ1.25 (t, 3H, J=7, CH₃), 2.44 (s, 3H, CH₃), 4.21 (q, 2H, J=7, CH₂), 7.42 (dt, 1H, J=4.8, 4.8, aromatic CH), 7.87 (dt, 1H, J=7.5, 8, aromatic CH), 8.22 (d, 1H, J=8, aromatic CH), 8.60 (d, 1H, J=4, aromatic CH), 11.13 (br s, 1H, NH), 11.38 (s, 1H, NH), 11.60 (s, 1H, NH), 12.58 (br s, 1H, NH).

Example 24

2-Acetylpyridine 5-[(2-pyridylamino)thiocarbonyl]thiocarbonohydrazone

Reaction of 2-acetylpyridine thiocarbonohydrazone, 1.53 g, and 2-pyridyl isothiocyanate (prepared by the method of A. E. S. Fairfull and D. A. Peak, J. Chem. Sot., 1955, page 796), 1.0 g, in 55 mL of DMF overnight gave 1.33 g (53%) of the title compound as a yellow powder, m.p. 204°–205° C. (dec.).

¹H-NMR: (DMSO-d₆) δ2.46 (s, 3H, CH₃), 2.72 and 2.88 (s, DMF), 7.08–8.63 (m, 8H, aromatic CH), 11.16 (s, 1H, NH), 11.27 (s, 1H, NH), 11.30 (s, 1H, NH), 11.34 (s, 1H, NH).

Example 25

2-Acetylpyridine 5-[(4-pyridylamino)thiocarbonyl]thiocarbonohydrazone

Reaction of 2-acetylpyridine thiocarbonohydrazone, 4.84 g, and 4-pyridyl isothiocyanate (prepared by the method of E. J. Hansen and H. J. Petersen, Synth. Commun., 1984, Vol. 14, page 537), 3.15 g, in 170 mL of dry DMF for 3 h gave 6.52 g (82%) of the title compound as a bright yellow powder, m.p. 179°–180° C. (dec.).

¹H-NMR: (DMSO-d₆) δ2.40 (s, 3H, CH₃), 2.71 and 2.87 (s, DMF), 7.33–8.59 (m, 8H, aromatic CH), 10.02 (s, 1H, NH), 10.27 (s, 1H, NH), 11.73 (s, 1H, NH), 13.43 (br s, 1H, NH).

Example 26

2-Acetylpyridine 5-[(4-methoxyanilino)thiocarbonyl]thiocarbonohydrazone

Reaction of 2-acetylpyridine thiocarbonohydrazone, 5.97 g, and 4-methoxyphenyl isothiocyanate (Trans World), 4.91 g, in 200 mL of dry DMF gave 7.13 g of an pale-yellow powder. Recrystallization from DMF/H2O afforded 6.63 g (62%) of the title compound as a yellow powder, m.p. 162°–164° C. (dec.).

¹H-NMR: (DMSO-d₆) δ2.40 (s, 3H, CCH₃), 3.72 (s, 3H, OCH₃), 6.86 (d, 2H, J=9, aromatic CH), 7.35 (m, 3H, aromatic CH), 7.80 (dt, 1H, J=2, 8, aromatic CH), 8.56 (d, 2H, J=3, aromatic CH), 9.70 (br s, 1H, NH), 9.72 (br s, 1H, NH), 10.45 (br s, 1H, NH), 10.88 (br s, 1H, NH).

Example 27

2-Formylpyridine 5-[(2-chloroanilino)thiocarbonyl]thiocarbonohydrazone

Reaction of 2-formylpyridine thiocarbonohydrazone, 7.47 g, and 2-chlorophenyl isothiocyanate (Aldrich), 6.5 g, in 200 mL of dry DMF for 1 h gave 12.26 g (84%) of the title compound as a white powder, m.p. 167°–168° C. (dec.).

¹H-NMR: (DMSO-d₆) δ3.14 (s, MeOH), 4.07 (br s, MeOH), 7.19–7.61 (m, 5H, aromatic CH), 7.84 (dt, 1H, J=1.4, 7.6, aromatic CH), 8.10 (s, 1H, aromatic CH), 8.35 (br s, 1H, NH), 8.55 (d, 1H, J=4, aromatic CH), 9.46 (br s, 1H, NH), 9.95 (br s, 1H, CHO), 10.63 (br s, 1H, NH), 12.14 (br s, 1H, NH).

Example 28

2-Formyl-6-methylpyridine 5-(2-chloroanilino)thiocarbonyl]thiocarbonohydrazone

Reaction of 2-formyl-6-methylpyridine thiocarbonohydrazone, 8.01 g, and 2-chlorophenyl isothiocyanate (Aldrich), 6.5 g, in 200 mL of dry DMF for 40 min gave 13.00 g (84%) of the title compound as a white powder, m.p. 151°–153° C. (dec.).

¹H-NMR: (DMSO-d₆) δ3.15 (s, MeOH), 4.07 (br s, MeOH), 2.46 (s, 3H, CH3), 7.27 (m, 3H, aromatic CH), 7.52 (m, 2H, aromatic CH), 7.72 (t, 1H, J=7.7, aromatic CH), 8.05 (s, 1H, NH), 8.21 (m, 1H, aromatic CH), 9.47

(br s, 1H, NH), 9.95 (br s, 1H, CHO), 10.60 (br s, 1H, NH), 12.12 (br s, 1H, NH).

Example 29

2-Acetylpyridine 5-[(2-chlorophenyl)carbamoyl]thiocarbonohydrazone

Reaction of 2-acetylpyridine thiocarbonohydrazone, 8.68 g, and 2-chlorophenyl isocyanate (Aldrich), 6.37 g, in 350 mL of dry DMF for 45 min gave a yellow powder. Recrystallization from 95% ethanol afforded 10.1 g (67%) of the title compound as an off-white powder, m.p. 177°–179° C. (dec.).

$^1$H-NMR: (DMSO-$d_6$) δ2.41 (s, 3H, CH$_3$), 7.00 (dt, 1H, J=2, 7.7, aromatic CH), 7.35 (m, 3H, aromatic CH), 7.80 (dt, 1H, J=2, 8, aromatic CH), 8.12 (dd, 1H, J=8.3, 1.5, aromatic CH), 8.34 (br s, 1H, NH), 8.56 (m, 2H, aromatic CH), 9.06 (br s, 1H, NH), 10.29 (br s, 1H, NH), 10.82 (br s, 1H, NH).

Example 30

2-(3-Methylbutyryl)pyridine 5[(2-chloroanilino)thiocarbonyl]thiocarbonohydrazone To a solution of isobutyl 2-pyridyl ketone [2-(3-methylbutyryl)pyridine, Alfred Bader Chemicals, Aldrich Chemical Co., Milwaukee, Wis., 53233], 4.06 g, in 150 mL of methanol was added thiocarbohydrazide (Sigma), 2.64 g. The resulting mixture was heated at reflux, under nitrogen, overnight. A precipitate was collected by filtration, washed with cold methanol, and dried to give 4.17 g of 2-(3-methylbutyryl)pyridine thiocarbonohydrazone. The crude material was dissolved in 100 mL of dry DMF and 2-chlorophenyl isothiocyanate (Trans World), 4.48 g, was added. The resulting mixture was stirred at RT for 45 min. The solution was cooled in an ice bath and H$_2$O was added. A precipitate was collected, washed with H$_2$O, and dried. Recrystallization from ether/hexane afforded 1.30 g (18%) of the title compound as yellow-orange crystals, m.p. 75° C. (dec., turned bright red and evolved H$_2$S to re-solidify and at 98°–101° C. decomposed again to give a dark red melt).

$^1$H-NMR: (DMSO-$d_6$) δ0.86 (d, 6H, J=6.6, CH$_3$); 1.98 (m, 1H, aliphatic CH), 3.06 (d, 2H, J=7.3, CH2), 7.34 (m, 5H, aromatic CH), 7.78 (m, 2H, aromatic CH), 8.56 (d, 1H, J=4.1, aromatic CH), 9.25–10.80 (br, 3H, NH), 10.91 (br s, 1H, NH).

Example 31

1,3-Dihydro-1-[5-[[1-(2-pyridyl)ethylidene]hydrazino]-1,3,4-thiadiazol2-yl]2H-benzimidazole-2-thione Reaction of 2-acetylpyridine thiocarbonohydrazone, 5.44 g, and 1,2-phenylene diisothiocyanate (Trans World), 5.00 g, in 200 mL of dry DMF overnight gave a white precipitate which was collected by filtration. The precipitate was heated at reflux in 200 mL of absolute ethanol for 2 days. A precipitate was collected by filtration, washed with cold ethanol, and dried to give 3.67 g (38%) of the title compound as a white powder, m.p. >280° C.

$^1$H-NMR: (DMS-$d_6$) δ2.42 (s, 3H, CH$_3$), 7.34 (m, 4H, aromatic CH), 7.87 (dt, 1H, J=2, 8, aromatic CH), 7.98 (d, 1H, J=8, aromatic CH), 8.38 (m, 1H, aromatic CH), 8.58 (m, 1H, aromatic CH).

Example 32

2-Acetylpyridine [5-(dimethylamino)-1,3,4-thiadiazol-2-yl]hydrazone

A solution of 2-acetylpyridine 5-[(dimethylamino)thiocarbonyl]thiocarbonohydrazone (European Patent 135713), 3.5 g, in 300 mL of 95% ethanol was heated at reflux for 20 h. stirred at RT for 72 h, and heated again at reflux for 24 h. The resulting yellow solution was concentrated in vacuo until a yellow solid appeared. The yellow solid was collected by filtration and combined with material collected from subsequent concentrations of the mother liquor. The combined solid was washed with cold 95% ethanol and dried in vacuo to give crude reaction produce, 1.84 g. The crude product was taken up in 200 mL of boiling 95% ethanol, filtered, and concentrated to a volume of 75 mL before cooling in an ice bath for 2 h. The yellow precipitate was collected by filtration, washed with cold 95% ethanol and dried in vacuo at 50° C. to give 1.31 g (37%) of the title compound as a yellow powder, m.p. 217°–217.5° C. (dec.).

$^1$H-NMR: (DMSO-$d_6$) δ2.32 (s., 3H, CCH$_3$), 2.96 (s, 6H, N(CH$_3$)$_2$), 7.32 (m, 1H, aromatic CH), 7.78 (dt, 1H, J=1.7, 7.4, aromatic CH), 7.93 (d, 1H, J=8, aromatic CH), 8.53 (d, 1H, J=5, aromatic CH), 11.30 (br s, 1H, NH).

Example 33

2-Acetylpyridine [5-(2-chloroanilino)-1,3,4-thiadiazol-2-yl]hydrazone

Triethylamine (Aldrich), 0.80 g, was added to a slurry of 2-acetylpyridine 5-[(2-chloroanilino)thiocarbonyl]thiocarbonohydrazone, 1.80 g, and 25 mL of dry methanol. The resulting yellow solution was heated at reflux for 4 days. A precipitate was collected by filtration, washed with cold methanol, and dried in vacuo to give 0.75 g (45%) of the title compound as an off-white powder, m.p. 238°–240° C. (dec.).

$^1$H-NMR: (DMSO-$d_6$) δ2.35 (s, 3H, CH$_3$), 7.00 (dt, 1H, J=1.5, 6.5, aromatic CH), 7.32 (m, 2H, aromatic CH), 7.44 (dd, 1H, J=1.4, 8, aromatic CH), 7.80 (dt, 1H, J=1.7, 8, aromatic CH), 7.93 (d, 1H, J=8, aromatic CH), 8.21 (br d, 1H, J=8, aromatic CH), 8.55 (m, 1H, aromatic CH), 9.24 (br s, 1H, NH), 11.46 (br s, 1H, NH).

Example 34

2-Acetylpyridine (4,5-dihydro-5-thioxo-1,3,4-thiadiazol-2-yl)hydrazone

A mixture of 2-acetylpyridine 5-[(dimethylamino)thiocarbonyl]thiocarbonohydrazone (European Patent 135713), 28.4 g, and 350 mL of trifluoroacetic acid (EM Science, Cherry Hill, N.J., 08034) was stirred at RT for 3 h. The resulting yellow solution was concentrated in vacuo, diluted with 700 mL of H$_2$O added over a 30 min period, and allowed to stand for 30 min while immersed in an ice bath. A yellow precipitate was collected by filtration, washed with cold H$^2$, and dried in vacuo to give 29.7 g of 2-acetylpyridine (4,5-dihydro-5-thioxo-1,3,4-thiadiazol-2-yl)hydrazone trifluoroacetate as a yellow crystalline solid. To a slurry of this material in 3 L of ethyl acetate was added 100 g of diisopropylethylamine (Aldrich) and the solid material dissolved to give a yellow solution. Within a short period of time, a white precipitate had formed. The mixture was allowed to stand for 1 h at RT and 1 h while immersed in an ice bath. The precipitate was collected by filtration. The filtrate was concentrated in vacuo to a volume of approximately 1 L and additional precipitate was collected by filtration. The collected solids were combined and dried in vacuo to give 15.45 g (58%) of the title compound as an off-white solid, m.p. 217.5°–218° C. (dec.). $^1$H-NMR: (DMSO-d$_6$) δ1.16 (t, EtOAc), 1.97 (s, EtOAc), 2.33 (s, 3H, CH$_3$), 4.01 (q, EtOAc), 7.36 (ddd, 1H, J=1.5, 5, 7, aromatic CH), 7.84 (m, 2H, aromatic CH), 8.56 (dt, 1H, J=1, 5, aromatic CH), 11.60 (br s, 1H, NH).

Example 35

2-Acetylpyridine [5-(methylthio)-1,3,4-thiadiazol-2yl]hydrazone

Method A

Carbon disulfide (4.0 mL, Aldrich) was added dropwise to a stirred mixture prepared from 87.5% potassium hydroxide (Mallinckrodt, Inc., Paris, Ky., 40361), 2.24 g, 2-acetylpyridine thiocarbonohydrazone, 7.00 g, and 220 mL of 9:1 methanol/water while the temperature was maintained below 30° C. with a water bath. After the yellow mixture had stirred at ambient temperature for 2.5 h, methyl iodide (Mallinckrodt), 2.26 g, was introduced dropwise and stirring was continued for 66 h. A precipitate was collected by filtration after 18 h and at the end of the reaction period. The first crop of solid collected was recrystallized from methanol, combined with the second crop of solid collected and dried in vacuo to give 2.73 g (31.2%) of the title compound as a light yellow needles, mp 230°–230.5° C. (dec.).

$^1$H-NMR: (DMSO-d$_6$) δ2.37 (s, 3H, COCH$_3$), 2.66 (s, 3H, SCH$_3$), 7.37 (m, 1H, aromatic CH), 7.88 (m, 2H, aromatic CH), 8.57 (m, 1H, aromatic CH), 11.85 (br s, 1H, NH).

Method B

Methyl iodide (Mallinckrodt), 0.60 mL (0.14 g), was added to a stirred solution prepared from 2-acetylpyridine (4,5-dihydro-5-thioxo-1,3,4-thiadiazol-2-yl)hydrazone, 0.25 g, 87.5% potassium hydroxide (Mallinckrodt), 57 mg, and 48 mL of methanol. A precipitate formed within 15 min. The mixture was stirred at ambient temperature for 18 h before the pale yellow solid was collected by filtration, washed with 20 mL of methanol and dried in vacuo (40° C.) to give 0.21 g (84%) of the title compound as a pale yellow solid, mp 230°–230.5° C. (dec.).

$^1$H-NMR: (DMSO-d$_6$) δ2.37 (s, 3H, COCH$_3$), 2.66 (s, 3H, SCH$_3$), 7.37 (m, 1H, aromatic CH), 7.87 (m, 2H, aromatic CH), 8.57 (m, 1H, aromatic CH), 11.90 (br s, 1H, NH).

The following compounds (examples 36–64) were prepared using the general method described in Example 12:

Example 36

2-Acetylpyridine 5-[(2-fluoroanilino)thiocarbonyl]thiocarbonohydrazone

Reaction of 2-acetylpyridine thiocarbonohydrazone, 7.00 g, and distilled 2-fluorophenyl isothiocyanate (Trans World), 5.11 g, in 245 mL of dry DMF for 1 h gave 15.03 g of a yellow solid. Recrystallization from DMF/H$_2$O afforded 10.06 g (83%) of the title compound as an orange powder, m.p. 140.7°–142.0° C. (dec.).

$^1$H-NMR: (DMSO-d$_6$) δ2.408 (s, 3H, CH$_3$), 7.106–7.254 (m, 4H, aromatic CH), 7.807 (dt, 1H, J=1.5, 8, aromatic CH), 8.571 (d, 2H, J=4, aromatic CH), 9.4.10 (br s, 1H, NH), 9.924 (br s, 1H, NH), 10.495 (br s, 1H, NH), 10.928 (s, 1H, NH).

Example 37

2-Acetylpyridine 5-[(2-iodoanilino)thiocarbonyl]thiocarbonohydrazone

Reaction of 2-acetylpyridine thiocarbonohydrazone, 7.00 g, and 2-iodophenyl isothiocyanate (Trans World), 9.17 g, in 250 mL of dry DMF for 2 h gave 14.52 g (92%) of the title compound as a pale yellow powder, m.p. 161.5°–162.7° C. (dec.).

$^1$H-NMR: (DMSO-d$_6$) δ2.413 (s, 3H, CH$_3$), 2.714 and 2.873 (s, DMF), 6.979 (t, 1H, J=7, aromatic CH), 7.334–7.412 (m, 2H, aromatic CH), 7.610 (d., 1H, J=3.5, aromatic CH), 7.764–7.862 (m, 2H, aromatic CH), 8.574 (d, 2H, J=5, aromatic CH), 9.375 (br s, 1H, NH), 9.900 (br s, 1H, NH), 10.525 (br s, 1H, NH), 10.950 (s, 1H, NH).

Example 38

2-Acetylpyridine 5-[(2-(trifluoromethyl)anilino)-thiocarbonyl]thiocarbonohydrazone Reaction of 2-acetylpyridine thiocarbonohydrazone, 7.00 g, and 2-(trifluoromethyl)phenyl isothiocyanate (Trans World), 7.14 g, in 250 mL of dry DMF gave 13.10 g (95%) of the title compound as a pale yellow powder, m.p. 118.8°–120.5° C. (dec.).

$^1$H-NMR: (DMSO-d$_6$) δ2.409 (s, 3H, CH$_3$), 2.713 and 2.873 (s, DMF), 7.356–7.479 (m, 2H, aromatic CH), 7.587–7.719 (m, 3H, aromatic CH), 7.815 (dt, 1H, J=2, 8, aromatic CH), 8.576 (d, 2H, J=4, aromatic CH), 9.325 (br s, 1H, NH), 9.950 (br s, 1H, NH), 10.550 (br s, 1H, NH), 10.963 (s, 1H, NH).

Example 39

2-Acetylpyridine 5-[(4-(trifluoromethyl)anilino)thiocarbonyl]thiocarbonohydrazone Reaction of 2-acetylpyridine thiocarbonohydrazone, 5.00 g, and 4-(trifluoromethyl)phenyl isothiocyanate (Trans World), 5.10 g, in 175 mL of dry DMF gave, after recrystallization from DMF/H$_2$O, 9.77 g (99%) of the title compound as a pale yellow powder, m.p. 165.5°–183.5° C. (dec.).

$^1$H-NMR: (DMSO-d$_6$) δ2.440 (s, 3H, CH$_3$), 2.734 and 2.894 (s, DMF), 7.389–7.429 (m, 1H, aromatic CH), 7.684 (d, 2H, J=8.5, aromatic CH), 7.750–7.854 (m, 3H, aromatic CH), 8.599 (d, 2H, J=4, aromatic CH), 9.883 (br s, 1H, NH), 10.063 (br s, 1H, NH), 10.500 (br s, 1H, NH), 11.022 (s, 1H, NH).

Example 40

2-Acetylpyridine 5-[(2,3-dichloroanilino)-thiocarbonyl]thiocarbonohydrazone

Reaction of 2-acetylpyridine thiocarbonohydrazone, 5.00 g, and distilled 2,3-dichlorophenyl isothiocyanate (Trans World), 5.12 g, in 180 mL of dry DMF gave, after recrystallization from DMF/H$_2$O, 11.13 g (98%) of the title compound as a yellow powder, m.p. 156.3°–157.5° C. (dec.).

$^1$H-NMR: (DMSO-d$_6$) δ2.409 (s, 3H, CH$_3$), 2.714 and 2.872 (s, DMF), 7.295–7.521 (m, 4H, aromatic CH), 7.807 (dt, 1H, J=2, 8, aromatic CH), 8.571 (d, 2H, J=4, aromatic CH), 9.555 (br s, 1H, NH), 10.029 (br s, 1H, NH), 10.519 (br s, 1H, NH), 10.955 (s, 1H, NH).

Example 41

2-Acetylpyridine 5-[(2,4-dichloroanilino)thiocarbonyl]thiocarbonohydrazone

Reaction of 2-acetylpyridine thiocarbonohydrazone, 6.65 g, and 2,4-dichlorophenyl isothiocyanate (Trans World), 6.81 g, in 230 mL of dry DMF gave, after recrystallization from DMF/H$_2$O, 12.65 g (96%) of the title compound as a yellow powder, m.p. 162.5°–164.0° C. (dec.).

$^1$H-NMR: (DMSO-d$_6$) δ2.427 (s, 3H, CH$_3$), 2.732 and 2.892 (s, DMF), 7.385–7.490 (m, 3H, aromatic CH), 7.638 (s, 1H, aromatic CH), 7.828 (dt, 1H, J=1,5, aromatic CH), 8.584–8.652 (m, 2H, aromatic CH), 9.486 (br s, 1H, NH), 10.077 (br s, 1H, NH), 10.536 (br s, 1H, NH), 11.005 (s, 1H, NH).

Example 42

2-Acetylpyridine 5-[(2,5-dichloroanilino)thiocarbonyl]thiocarbonohydrazone

Reaction of 2-acetylpyridine thiocarbonohydrazone, 5.50 g, and distilled 2,5-dichlorophenyl isothiocyanate (Trans World), 5.63 g, in 200 mL of dry DMF gave, after recrystallization from DMF/H$_2$O, 11.67 g (96%) of the title compound as a yellow powder, m.p. 119°–121° C. (dec.).

$^1$H-NMR: (DMSO-d$_6$) δ2.41 (s, 3H, CH3), 2.71 and 2.87 (s, DMF), 7.28–7.64 (m, 4H, aromatic CH), 7.82 (t, 1H, J=8, aromatic CH), 8.58 (d, 2H, J=4, aromatic CH), 9.47 (br s, 1H, NH), 10.13 (br s, 1H, NH), 10.53 (br s, 1H, NH), 11.00 (s, 1H, NH).

Example 43

2-Acetylpyridine 5-[(3,4-dichloroanilino)thiocarbonyl]thiocarbonohydrazone

Reaction of 2-acetylpyridine thiocarbonohydrazone, 5.50 g, and distilled 3,4-dichlorophenyl isothiocyanate (Trans World), 5.63 g, in 200 mL of dry DMF gave, after recrystallization from DMF/H$_2$O, 10.57 g (97%) of the title compound as a yellow powder, m.p. 167°–168° C. (dec.).

$^1$H-NMR: (DMSO-d$_6$) δ2.42 (s, 3H, CH$_3$), 2.71 and 2.87 (s, DMF), 7.37 (t, 1H, J=3, aromatic CH), 7.55 (s, 2H, aromatic CH), 7.76–7.94 (m, 2H, aromatic CH), 8.58 (d, 2H, J=4, aromatic CH), 9.81 (br s, 1H, NH), 10.06 (br s, 1H, NH), 10.47 (br s, 1H, NH), 10.99 (s, 1H, NH).

Example 44

2-Acetylpyridine 5-[(3,5-dichloroanilino)thiocarbonyl]thiocarbonohydrazone

Reaction of 2-acetylpyridine thiocarbonohydrazone, 5.50 g, and 3,5-dichlorophenyl isothiocyanate (Trans World), 5.63 g, in 200 mL of dry DMF gave, after recrystallization from DMF/H$_2$O, 10.47 g (96%) of the title compound as a yellow powder, m.p. 184.5°–186.0° C. (dec.).

$^1$H-NMR: (DMSO-d$_6$) d 2.43 (s, 3H, CH$_3$), 2.72 and 2.88 (s, DMF), 7.33–7.43 (m, 2H, aromatic CH), 7.73–7.86 (m, 3H, aromatic CH), 8.59 (d, 2H, J=3, aromatic CH), 9.83 (br s, 1H, NH), 10.14 (br s, 1H, NH), 10.47 (br s, 1H, NH), 11.02 (s, 1H, NH).

Example 45

2-Acetylpyridine 5-[(2,3,4-trichloroanilino)-thiocarbonyl]thiocarbonohydrazone

Reaction of 2-acetylpyridine thiocarbonohydrazone, 5.50 g, and 2,3,4-trichlorophenyl isothiocyanate (Trans World), 6.58 g, in 200 mL of dry DMF gave, after recrystallization from DMF/H$_2$O, 12.66 g (97%) of the title compound as a yellow powder, m.p. 250° C. (decompose at 130° C.

$^1$H-NMR: (DMSO-d$_6$) δ2.41 (s, 3H, CH$_3$), 2.72 and 2.88 (s, DMF), 7.36–7.46 (m, 2H, aromatic CH), 7.65 (d, 2H, J=8, aromatic CH), 7.82 (dt, 1H, J=2, 8, aromatic CH), 8.57–8.64 (m, 2H, aromatic CH), 9.62 (br s, 1H, NH), 10.12 (br s, 1H, NH), 10.53 (br s, 1H, NH), 10.98 (s, 1H, NH).

Example 46

2-Acetylpyridine 5-[(2,4,5-trichloroanilino)thiocarbonyl]thiocarbonohydrazone

Reaction of 2-acetylpyridine thiocarbonohydrazone, 5.50 g, and 2,4,5-trichlorophenyl isothiocyanate (Trans World), 6.58 g, in 200 mL of dry DMF gave, after recrystallization from DMF/H$_2$O, 13.37 g (100%) of the title compound as a yellow powder, m.p. 133.5°–135.5° C. (dec.).

$^1$H-NMR: (DMSO-d$_6$) δ2.42 (s, 3H, CH$_3$), 2.72 and 2.88 (s, DMF), 7.40 (dt, 1H, J=1, 6, aromatic CH), 7.77–7.89 (m, 2H, aromatic CH), 8.58 (d, 2H, J=3.5, aromatic CH), 9.52 (s, 1H, aromatic CH), 10.19 (br s, 1H, NH), 10.53 (br s, 1H, NH), 10.74 (br s, 1H, NH), 11.00 (s, 1H, NH).

Example 47

2-Acetylpyridine 5-[(3-iodoanilino)thiocarbonyl]thiocarbonohydrazone

Reaction of 2-acetylpyridine thiocarbonohydrazone, 6.00 g, and 3-iodophenyl isothiocyanate (Trans World), 7.86 g, in 225 mL of dry DMF for 1 h gave, after recrystallization from DMF/H$_2$O, 13.00 g (96%) of the title compound as a pale yellow powder, m.p. 159.5°–161.0° C. (dec.).

$^1$H-NMR: (DMSO-d$_6$) δ2.42 (s, 3H, CH$_3$), 7.10 (t, 1H, J=6, aromatic CH), 7.35–7.59 (m, 4H, aromatic CH), 7.81 (dt, 1H, J=1.7, 8, aromatic CH), 8.58 (d, 2H,, J=5, aromatic CH), 9.71 (br s, 1H, NH), 9.94 (br s, 1H, NH), 10.47 (br s, 1H, NH), 10.94 (s, 1H, NH).

Example 48

2-Acetylpyridine 5-[(4-iodoanilino)thiocarbonyl]thiocarbonohydrazone

Reaction of 2-acetylpyridine thiocarbonohydrazone, 5.50 g, and 4-iodophenyl isothiocyanate (Trans World), 7.21 g, in 200 mL of dry DMF for 1 h gave, after recrystallization from DMF/H$_2$O, 12.04 g (97%) of the title compound as a pale yellow powder, m.p. 173.5°–174.5° C. (dec.).

$^1$H-NMR: (DMSO-d$_6$) δ2.41 (s, 3H, CH$_3$), 2.72 and 2.87 (s, DMF), 7.29–7.41 (m, 3H, aromatic CH), 7.64 (d, 2H, J=8.6, aromatic CH), 7.81 (dt, 1H, J=1.5, 8, aromatic CH), 8.50–8.60 (m, 2H, aromatic CH), 9.70 (br s, 1H, NH), 9.92 (br s, 1H, NH), 10.46 (br s, 1H, NH), 10.95 (s, 1H, NH).

Example 49

2-Acetylpyridine 5-[(3-fluoroanilino)thiocarbonyl]thiocarbonohydrazone

Reaction of 2-acetylpyridine thiocarbonohydrazone, 7.00 g, and 3-fluorophenyl isothiocyanate (Aldrich), 4.23 g, in 200 mL of dry DMF for 1 h gave, after recrystallization from DMF/$H_2O$, 9.09 g (95%) of the title compound as a yellow powder, m.p. 161.0°–162.5° C. (dec.).

$^1$H-NMR: (DMSO-$d_6$) δ2.42 (s, 3H, $CH_3$), 2.72 and 2.87 (s, DMF), 6.91–6.99 (m, 1H, aromatic CH), 7.30–7.62 (m, 4H, aromatic CH), 7.81 (dt, 1H, J=2, 8, aromatic CH), 8.50–8.59 (m, 2H, aromatic CH), 9.79 (br s, 1H, NH), 9.98 (br s, 1H, NH), 10.51 (br s, 1H, NM), 10.95 (s, 1H, NH).

Example 50

2-Acetylpyridine 5-[(4-fluoroanilino)thiocarbonyl]thiocarbonohydrazone

Reaction of 2-acetylpyridine thiocarbonohydrazone, 7.00 g, and 4-fluorophenyl isothiocyanate (Aldrich), 4.53 g, in 210 mL of dry DMF gave, after recrystallization from DMF/$H_2O$, 9.04 g (95%) of the title compound as a yellow powder, m.p. 158.5°–159.5° C. (dec.).

$^1$H-NMR: (DMSO-$d_6$) δ2.41 (s, 3H, $CH_3$), 2.72 and 2.87 (s, DMF), 7.14 (t, 2H, J=8.9, aromatic CH), 7.35–7.49 (m, 3H, aromatic CH), 7.80 (dt, 1H, J=1.8, 7.7, aromatic CH), 8.51–8.58 (m, 2H, aromatic CH), 9.71 (br s, 1H, NH), 9.86 (br s, 1H, NH), 10.48 (br s, 1H, NH), 10.91 (s, 1H, NH).

Example 51

2-Acetylpyridine 5-[(3-bromoanilino)thiocarbonyl]thiocarbonohydrazone

Reaction of 2-acetylpyridine thiocarbonohydrazone, 5.50 g, and 3-bromophenyl isothiocyanate (Aldrich), 5.91 g, in 200 mL of dry DMF for 0.75 h gave, after recrystallization from DMF/$H_2O$, 11.08 g (99%) of the title compound as a yellow powder, m.p. 161.5°–165.0° C. (dec.).

$^1$H-NMR: (DMSO-$d_6$) δ2.41 (s, 3H, $CH_3$), 2.71 and 2.87 (s, DMF), 7.26–7.55 (m, 4H, aromatic CH), 7.81 (t, 1H, J=8, aromatic CH), 8.58 (d, 2H, J=4, aromatic CH), 9.76 (br s, 1H, NH), 9.98 (br s, 1H, NH), 10.46 (br s, 1H, NH), 10.97 (s, 1H, NH).

Example 52

2-Acetylpyridine 5-[(4-bromoanilino)thiocarbonyl]thiocarbonohydrazone

Reaction of 2-acetylpyridine thiocarbonohydrazone, 7.00 g, and 4-bromophenyl isothiocyanate (Aldrich), 7.52 g, in 250 mL of dry DMF for 1 h gave, after recrystallization from DMF/$H_2O$, 13.86 g (98%) of the title compound as a yellow powder, m.p. 167.0°–168.5° C. (dec.).

$^1$H-NMR: (DMSO-$d_6$) δ2.41 (s, 3H, $CH_3$), 2.71 and 2.81 (s, DMF), 7.35–7.54 (m, 5H, aromatic CH), 7.81 (dt, 1H, J=2, 4, aromatic CH), 8.57 (d, 2H, J=4, aromatic CH), 9.73 (br s, 1H, NH), 9.92 (br s, 1H, NH), 10.48 (br s, 1H, NH), 10.94 (s, 1H, NH).

Example 53

2-Acetylpyridine 5-[(2-methylanilino)thiocarbonyl]thiocarbonohydrazone

Reaction of 2-acetylpyridine thiocarbonohydrazone, 5.50 g, and distilled 2-methylphenyl isothiocyanate (Aldrich), 4.12 g, in 200 mL of dry DMF for 1.5 h gave, after recrystallization from DMF/$H_2O$, 7.14 g (76%) of the title compound as a yellow powder, m.p. 168.5°–175.5° C. (dec.).

$^1$H-NMR: (DMSO-$d_6$) δ2.23 (s, 3H, $CH_3$), 2.40 (s, 3H, $CH_3$), 7.15 (br s, 4H, aromatic CH), 7.38 (t, 1H, J=6, aromatic CH), 7.81 (dt, 1H, J=1.8, 8, aromatic CH), 8.58 (d, 2H, J=5, aromatic CH), 9.40 (br s, 1H, NH), 9.73 (br s, 1H, NH), 10.47 (br s, 1H, NH), 10.88 (s, 1H, NH).

Example 54

2-Acetylpyridine 5-[(3-methylanilino)thiocarbonyl]thiocarbonohydrazone

Reaction of 2-acetylpyridine thiocarbonohydrazone, 5.50 g, and distilled 3-methylphenyl isothiocyanate (Aldrich), 4.12 g, in 200 mL of dry DMF for 1.5 h gave, after recrystallization from DMF/$H_2O$, 9.47 g (98%) of the title compound as a yellow powder, m.p. 173.5°–177.0° C. (dec.).

$^1$H-NMR: (DMSO-$d_6$) δ 2.28 (s, 3H, $CH_3$), 2.40 (s, 3H, $CH_3$), 2.72 and 2.88 (s, DMF), 6.95 (d, 1H, J=7, aromatic CH), 7.15–7.42 (m, 4H, aromatic CH), 7.82 (t, 1H, J=8, aromatic CH), 8.51–8.59 (m, 2H, aromatic CH), 9.67 (br s, 1H, NH), 9.82 (br s, 1H, NH), 10.49 (br s, 1H, NH), 10.93 (s, 1H, NH).

Example 55

2-Acetylpyridine 5-[(4-methylanilino)thiocarbonyl]thiocarbonohydrazone

Reaction of 2-acetylpyridine thiocarbonohydrazone, 7.00 g, and p-tolyl isothiocyanate (Aldrich), 5.24 g, in 250 mL of dry DMF gave, after recrystallization from DMF/$H_2O$, 10.90 g (91%) of the title compound as a yellow powder, m.p. 154.0°–155.5° C. (dec.).

1H-NMR: (DMSO-$d_6$) δ2.28 (s, 3H, $CH_3$), 2.43 (s, 3H, $CH_3$), 2.74 and 2.90 (s, DMF), 7.13 (d, 2H, J=8, aromatic CH), 7.35–7.43 (m, 3H, aromatic CH), 7.83 (dt, 1H, J=2, 8, aromatic CH), 8.59 (d, 2H, J=4, aromatic CH), 9.60 (br s, 1H, NH), 9.77 (br s, 1H, NH), 10.50 (br s, 1H, NH), 10.93 (s, 1H, NH).

Example 56

2-Acetylpyridine 5-[(4-chloro-2-methylanilino)thiocarbonyl]thiocarbonohydrazone

Reaction of 2-acetylpyridine thiocarbonohydrazone, 7.00 g, and 4-chloro-2-methylphenyl isothiocyanate (Trans World), 6.45 g, in 250 mL of dry DMF for 1.5 h gave, after recrystallization from DMF/$H_2O$, 11.58 g (88%) of the title compound as a yellow powder, m.p. 165.5°–166.5° C. (dec.).

$^1$H-NMR: (DMSO-$d_6$) δ2.22 (s, 3H, $CH_3$), 2.20 (s, 3H, $CH_3$), 2.72 and 2.88 (s, DMF), 7.14–7.27 (m, 3H, aromatic CH), 7.34–7.41 (m, 1H, aromatic CH), 7.81 (dt, 1H, J=2, 8, aromatic CH), 8.57 (d, 2H, J=4, aromatic CH), 9.40 (s, 1H, NH), 9.81 (br s, 1H, NH), 10.45 (br s, 1H, NH), 10.88 (s, 1H, NH).

Example 57

2-Acetylpyridine 5-[(2-chloro-4-methylanilino)thiocarbonyl]thiocarbonohydrazone Reaction of 2-acetylpyridine thiocarbonohydrazone, 5.50 g, and distilled 2-chloro-4-methylphenyl isothiocyanate (Trans World), 5.07 g, in 200 mL of dry DMF for 0.75 h gave, after recrystallization from DMF/$H_2O$, 9.86 g (95%) of the title compound as a yellow powder, m.p. 161°–162° C. (dec.).

$^1$H-NMR: (DMSO-$d_6$) δ2.28 (s, 3H, $CH_3$), 2.41 (s, 3H, $CH_3$), 2.72 and 2.88 (s, DMF), 7.12 (d, 1H, J=8, aromatic CH), 7.29–7.47 (m, 3H, aromatic CH), 7.81 (dt, 1HδJ=1.8, 8, aromatic CH), 8.58 (d, 2H, J=5, aromatic CH), 9.3,2 (s, 1H, NH), 9.89 (br s, 1H, NH), 10.50 (br s, 1H, NH), 10.94 (s, 1H, NH).

Example 58

2-Acetylpyridine 5-[(3-chloro-4-methylanilino)thiocarbonyl]thiocarbonohydrazone Reaction of 2-acetylpyridine thiocarbonohydrazone, 5.50 g, and distilled 3-chloro-4-methylphenyl isothiocyanate (Trans World), 5.07 g, in 200 mL of dry DMF for 0.75 h gave, after recrystallization from DMF/$H_2O$, 10.13 g (98%) of the title compound as a yellow powder, m.p. 165°–166° C. (dec.).

$^1$H-NMR: (DMSO-$d_6$) δ2.28 (s, 3H, $CH_3$), 2.42 (s, 3H, $CH_3$), 2.72 and 2.88 (s, DMF), 7.25–7.42 (m, 3H, aromatic CH), 7.62 (br s, 1H, aromatic CH), 7.81 (dt, 1H, J=1.7, 8, aromatic CH), 8.58 (d, 2H, J=4, aromatic CH), 9.71 (s, 1H, NH), 9.92 (br s, 1H, NH), 10.47 (br s, 1H, NH), 10.95 (s, 1H, NH).

Example 59

2-Acetylpyridine 5-[(5-chloro-2-methylanilino)thiocarbonyl]thiocarbonohydrazone Reaction of 2-acetylpyridine thiocarbonohydrazone, 8.61 g, and distilled 5-chloro-2-methylphenyl isothiocyanate (Trans World), 7.93 g, in 200 mL of dry DMF for 0.75 h gave, after recrystallization from DMF/$H_2O$, 16.58 g (81%) of the title compound as a pale yellow powder, m.p. 134°–135° C. (dec.).

$^1$H-NMR: (DMSO-$d_6$) δ2.19 (s, 3H, $CH_3$), 2.40 (s, 3H, $CH_3$), 2.72 and 2.88 (s, DMF), 7.20 (m, 3H, aromatic CH), 7.40 (t, 1H, J=5, aromatic CH), 7.81 (dt, 1H, J=2, 8, aromatic CH), 8.56 (d, 2H, J=4, aromatic CH), 9.47 (s, 1H, NH), 9.90 (br s, 1H, NH), 10.46 (br s, 1H, NH), 10.95 (s, 1H, NH).

Example 60

2-Acetylpyridine 5-[(5-chloro-2-methoxyanilino)thiocarbonyl]thiocarbonohydrazone Reaction of 2-acetylpyridine thiocarbonohydrazone, 5.50 g, and 5-chloro-2-methoxyphenylisothiocyanate (Trans World), 5.51 g, in 200 mL of dry DMF for 1 h gave, after recrystallization from DMF/$H_2O$, 9.39 g (87%) of the title compound as a yellow powder, m.p. 156.5°–158° C. (dec.).

$^1$H-NMR: (DMSO-$d_6$) δ2.43 (s, 3H, $CH_3$), 2.72 and 2.87 (s, DMF), 3.76 (br s, 3H, OCH3), 7.02–7.18 (m, 2H, aromatic CH), 7.36–7.43 (m, 1H, aromatic CH), 7.83 (dt, 1H, J=2, 8, aromatic CH), 8.41–8.60 (m, 2H, aromatic CH), 8.99 (br s, 1H, aromatic CH), 9.58 (s, 1H, NH), 10.12 (br s, 1H, NH), 10.65 (br s, 1H, NH), 11.03 (s, 1H, NH).

Example 61

2-Acetylpyridine 5-[(3-chloro-2-methoxyanilino)thiocarbonyl]thiocarbonohydrazone Reaction of 2-acetylpyridine thiocarbonohydrazone, 8.09 g, and distilled 3-chloro-2-methoxyphenyl isothiocyanate (Trans World), 5.51 g, in 200 mL of dry DMF for 45 minutes gave, after recrystallization from DMF/$H_2O$, 15.64 g (99%) of the title compound as a pale yellow powder, m.p. 170°–171° C. (dec.).

$^1$H-NMR: (DMSO-$d_6$) δ2.42 (s, 3H, $CH_3$), 3.76 (br s, 3H, $OCH_3$), 7.06–7.14 (t, 1H, J=8, aromatic CH), 7.25–7.43 (m, 2H, aromatic CH), 7.76–7.84 (m, 2H, aromatic CH), 8.57 (d, 2H, J=4.6, aromatic CH), 9.25 (br s, 1H, aromatic CH), 10.09 (s, 1H, NH), 10.56 (br s, 1H, NH), 11.05 (br s, 1H, NH).

Example 62

2-Acetylpyridine 5-[(3-chloro-2-fluoroanilino)thiocarbonyl]thiocarbonohydrazone Reaction of 2-acetylpyridine thiocarbonohydrazone, 5.31 g, and distilled 3-chloro-2-fluorophenyl isothiocyanate (Trans World), 5.00 g, in 200 mL of dry DMF for 45 minutes gave, after recrystallization from DMF/$H_2O$, 10.69 g (93%) of the title compound as a yellow powder, m.p. 171°–174° C. (dec.).

$^1$H-NMR: (DMSO-$d_6$) δ2.41 (s, 3H, $CH_3$), 2.71 and 2.87 (s, DMF), 7.30–7.50 (m, 3H, aromatic CH), 7.81 (t, 2H, J=8, aromatic CH), 8.58 (d, 2H, J=4, aromatic CH), 9.77 (br s, 1H, aromatic CH), 10.00 (s, 1H, NH), 10.47 (br s, 1H, NH), 10.97 (br s, 1H, NH).

Example 63

2-Acetylpyridine 5-[(4-chloro-3-nitroanilino)thiocarbonyl]thiocarbonohydrazone Reaction of 2-acetylpyridine thiocarbonohydrazone, 5.50 g, and 4-chloro-3-nitrophenyl isothiocyanate (Trans World), 5.92 g, in 200 mL of dry DMF for 1 h gave, after recrystallization from DMF/$H_2O$, 12.95 g (97%) of the title compound as a yellow-green powder, m.p. 151.5°–172.5° C. (dec.).

$^1$H-NMR: (DMSO-$d_6$) δ2.43 (s, 3H, $CH_3$), 2.72 and 2.88 (s, DMF), 7.36–7.42 (m, 1H, aromatic CH), 7.70 (d, 1H, J=8, aromatic CH), 7.82 (dt, 1H, J=1.5, 8, aromatic CH), 8.58 (d, 2H, J=5, aromatic CH), 10.01 (br s, 1H, aromatic CH), 10.20 (s, 1H, NH), 10.48 (br s, 1H, NH), 11.02 (br s, 1H, NH).

Example 64

2-Acetylpyridine5-[(3-pyridylamino)thiocarbonyl]thiocarbonohydrazone

Reaction of 2-acetylpyridine thiocarbonohydrazone, 18.38 g, and 3-pyridyl isothiocyanate (prepared by the method of J. C. Jochims, Chem. Ber., 1968, Vol. 101, page 1746), 12.0 g, in 660 mL of DMF overnight gave 24.00 g (79%) of the title compound as a yellow powder, m.p. 176°–179° C. (dec.).

$^1$H-NMR: (DMSO-d$_6$) δ2.42 (s, 3H, CH$_3$), 2.72 and 2.87 (s, DMF), 7.38 (m, 2H, aromatic CH), 7.81 (m, 2H, aromatic CH), 8.31 (d, 1H, J=4, aromatic CH), 8.57 (d, 3H, J=4, aromatic CH), 9.81 (s, 1H, NH), 10.02 (s, 1H, NH), 10.50 (s, 1H, NH), 10.97 (s, 1H, NH).

The following compound (example 65) was prepared using the general method described in preparation 4:

Example 65

2-Acetylpyridine5-[(2,6-dichloroanilino)thiocarbonyl]-thiocarbonohydrazone

In a 2 L 3-neck flask, reaction of 2-acetylpyridine thiocarbonohydrazone, 7.39 g, and 2,6-dichlorophenyl isothiocyanate (Trans World), 7.00 g, in 1 L of absolute ethanol gave for 45 min 9.77 g (60%) of the title compound as a yellow powder, m.p. 162.5°–164.0° C. (dec.).

$^1$H-NMR: (DMSO-d$_6$) δ3.40 (s, 3H, CH$_3$), 7.23–7.46 (m, 4H, aromatic CH), 7.81 (t, 1H, J=7.7, aromatic CH), 8.56 (d, 2H, J=4.4, aromatic CH), 9.55 (br s, 1H, NH), 9.94 (br s, 1H, NH), 10.46 (br s, 1H, NH), 10.89 (s, 1H, NH).

Example 66

2-Acetylpyridine[5-(2,3-dichloroanilino)-1,3,4-thiadiazol-2-yl]hydrazone

Hydrogen peroxide (Aldrich), 210 μL, was added to a mixture of 2-acetylpyridine 5-[(2,3-dichloroanilino)-thiocarbonyl]thiocarbonohydrazone, 0.188 g, dry triethylamine (Aldrich), 500 μL, and 15 mL of dry methanol. The resulting mixture was stirred at RT for 40 min. A precipitate was collected by filtration, washed with cold methanol, and dried in vacuo to give 0.112 g (76%) of the title compound as a yellow-orange powder, m.p. 244.5°–245° C. (dec.).

$^1$H-NMR: (DMSO-d$_6$) δ2.36 (s, 3H, CH$_3$), 7.26–7.38 (m, 3H, aromatic CH), 7.77–7.96 (m, 2H, aromatic CH), 8.25 (d, 1H, J=8, aromatic CH), 8.57 (d, 1H, J=4, aromatic CH), 9.49 (br s, 1H, NH), 11.53 (br s, 1H, NH).

Example 67

2-Acetylpyridine[5-(2,4-dichloroanilino)-1,3,4-thiadiazol-2-yl]hydrazone

Hydrogen peroxide (Aldrich), 210 μL, was added to a mixture of 2-acetylpyridine 5-[(2,4-dichloroanilino)-thiocarbonyl]thiocarbonohydrazone, 0.271 g, dry triethylamine (Aldrich), 500 μL, and 15 mL of dry methanol. The resulting mixture was stirred at RT for 45 min. A precipitate was collected by filtration, washed with cold methanol, and dried in vacuo to give 0.188 g (76%) of the title compound as an orange powder, m.p. 248°–249° C. (dec.).

$^1$H-NMR: (DMSO-d$_6$) δ2.35 (s, 3H, CH$_3$), 7.30–7.43 (m, 2H, aromatic CH), 7.58 (d, 1H, J=2, aromatic CH), 7.78–7.95 (m, 2H, aromatic CH), 8.33 (d, 1H, J=10, aromatic CH), 8.55 (d, 1H, J=5, aromatic CH), 9.40 (br s, 1H, NH), 11.50 (br s, 1H, NH).

Example 68

2-Acetylpyridine[5-(4-(trifluoromethyl)anilino)-1,3,4-thiadiazol-2-yl]hydrazone

Hydrogen peroxide (Aldrich), 210 μL, was added to a mixture of 2-acetylpyridine 5-[(4-(trifluoromethyl)anilino)thiocarbonyl]thiocarbonohydrazone, 0.233 g, dry triethylamine (Aldrich), 500 μL, and 15 mL of dry methanol. The resulting mixture was stirred at RT for 50 min. A precipitate was collected by filtration, washed with cold methanol, and dried in vacuo to give 0.106 g (50%) of the title compound as an off-white powder, m.p.>250° C.

$^1$H-NMR: (DMSO-d$_6$) δ2.35 (s, 3H, CH$_3$), 7.31–7.91 (m, 7H, aromatic CH), 10.27 (br s, 1H, NH), 11.58 (br s, 1H, NH).

Pharmaceutical Formulations

In the following Examples, the antiviral compound is acyclovir and the RR inhibitor is 2-acetylpyridine(4,5-dihydro-5-thioxo-1,3,4-thiadiazol-2-yl)hydrazone.

| Tablet | Amount |
| --- | --- |
| RR Inhibitor | 300 mg |
| AntiviralCompound | 500 mg |
| Lactose | 105 mg |
| Starch | 50 mg |
| Polyvinylpyrrolidinone | 20 mg |
| Magnesium Stearate | 10 mg |
| | 985 mg |

The active compounds are mixed with the lactose and starch and are wet granulated with a solution of the polyvinylpyrrolidinone. The granules are dried, sifted, and blended with magnesium stearate and compressed.

| Capsule | Amount |
| --- | --- |
| RR Inhibitor | 300 mg |
| Antiviral Compound | 500 mg |
| Lactose | 100 mg |
| Sodium Starch Glycollate | 10 mg |
| Polyvinylpyrrolidinone | 10 mg |
| Magnesium Stearate | 3 mg |
| | 923 mg |

The active compounds are mixed with the lactose and sodium starch glycollate and are wet granulated with a solution of the polyvinylpyrrolidinone. The granules are dried, sifted, and blended with the magnesium stearate and filled into hard gelatin capsules.

| Cream (1) | Amount |
| --- | --- |
| RR Inhibitor | 6.00 g |
| Antiviral Compound | 10.00 g |
| Glycerol | 2.00 g |
| Cetostearyl Alcohol | 6.75 g |
| Sodium Lauryl Sulfate | 0.75 g |
| White Soft Paraffin | 12.50 g |
| Liquid Paraffin | 5.00 g |
| Chlorocresol | 0.10 g |
| Purified Water to | 100.00 g |

The active compounds are mixed with purified water and glycerol and heated to 70° C. The remaining ingredients are heated together at 70° C. The two parts are added together and emulsified. The cream is cooled and filled into containers.

| Cream (2) | Amount |
| --- | --- |
| RR Inhibitor | 6.00 g |
| Antiviral Compound | 10.00 g |
| Mineral Oil, Heavy | 5.00 g |
| Polawax | 7.50 g |
| Propylene Glycol | 40.00 g |
| White Petrolatum | 12.50 g |
| Sodium Edetate | 0.10 g |

| -continued | |
| --- | --- |
| Cream (2) | Amount |
| Purified Water to | 100.00 g |

A solution of sodium edetate in water is heated to 70°–75° C. and added to a mixture of the mineral oil, white petrolatum and polawax, heated to the same temperature. The propylene glycol is added and the mixture is allowed to cool to 50°–55° C. The two active compounds are added, mixed and allowed to cool to 25°–30° C. Sufficient purified water is added to achieve the proper batch weight. The cream is filled into containers.

| Intravenous Injection | Amount |
| --- | --- |
| RR Inhibitor | 300 mg |
| Antiviral Compound | 500 mg |
| Glycerol | 200 mg |
| Sodium Hydroxide solution qs | pH 7.0-7.5 |
| Water for Injections to | 10 mL |

The active compounds and the mannitol are dissolved in a part of the water for injections. The pH is adjusted with the sodium hydroxide solution and the solution is made up to volume with additional water for injections. Under aseptic conditions, the solution is sterilized by filtration and filled into sterile vials. Water is removed by freeze-drying. The vials are sealed under an atmosphere of nitrogen and are closed with a sterile closure and a metal collar.

We claim:

1. A compound selected from the group consisting of
   (a) 2-Acetylpyridine 5-((4-Chloroanilino)Thiocarbonyl) Thiocarbonohydrazone;
   (b) 2-Acetylpyridine 5-((2-Methoxy-5-Nitroanilino) Thiocarbonyl)Thiocarbonohydrazone;
   (c) 2-Formylpyridine 5-((2-Chloroanilino)Thiocarbonohydrazone;
   (d) 2-(3-Methylbutyryl)Pyridine 5-((2-Chloroanilino)Thiocarbonyl)Thiocarbonohydrazone;
   (e) 2-Acetylpyridine 5-((3-Chloroanilino)Thiocarbonyl)Thiocarbonohydrazone;
   (f) 2-Acetylpyridine 5-((2-Iodoanilino)Thiocarbonyl)Thiocarbonohydrazone;
   (g) 2-Acetylpyridine 5-((4- (Trifluromethyl)Anilino) Thiocarbonyl)Thiocarbonohydrazone;
   (h) 2-Acetylpyridine 5-((2,3-Dichloroanilino)Thiocarbonyl)Thiocarbonohydrazone;
   (i) 2-Acetylpyridine 5-((3-Iodoanilino)Thiocarbonyl)Thiocarbonohydrazone;
   (j) 2-Acetylpyridine 5-((4-Chloro-2-Methylanilino)-Thiocarbonyl)Thiocarbonohydrazone;
   (k) 2-Acetylpyridine 5-((4-Bromoanilino)Thiocarbonyl)Thiocarbonohydrazone
   (l) 2-Acetylpyridine 5-((5-Chloro-2-Methoxyanilino)-Thiocarbonyl)Thiocarbonohydrazone;
   (m) 2-Acetylpyridine 5-((2,5-Dichloroanilino)Thiocarbonyl)Thiocarbonohydrazone;
   (n) 2-Acetylpyridine 5-((4-Chloro-3-Nitroanilino)-Thiocarbonyl)Thiocarbonohydrazone;
   and
   (o) 2-Acetylpyridine 5-((2,4,5-Trichloroanilino)Thiocarbonyl)Thiocarbonohydrazone.

2. A pharmaceutically acceptable salt of a compound of claim 1.

3. A compound selected from the group consisting of:
   (a) 2-ACETYLPYRIDINE 5-(((MORPHOLINOETHYL)AMINO) THIOCARBONYL)THIOCARBONOHYDRAZONE,
   (b) 2-ACETYLPYRIDINE 5-((2-CHLOROANILINO)THIOCARBONYL) THIOCARBONOHYDRAZONE 1-OXIDE,
   (c) 3-(1-(((1(2-PYRIDYL)ETHYLIDENE(HYDRAZINO)THIOCARBONYL)-4-THIOSEMICARBAZIDO)BENZONITRILE,
   (d) 3-(1-(((1-(2-PYRIDYL)ETHYLIDENE)HYDRAZINO)THIOCARBONYL)-THIOSEMICARBAZIDO)BENZOIC ACID,
   (e) 2-ACETYLPYRIDINE 5-(1-ADAMANTANYLAMINO) THIOCARBONYL)THIOCARBONOHYDRAZONE,
   (f) 2-ACETYLPYRIDINE 5-(((2-(2-PYRIDYL)ETHYL)AMINO) THIOCARBONYL) THIOCARBONOHYDRAZONE,
   (g) 2-ACETYLPYRIDINE 5-((4-METHOXYANILINO) THIOCARBONYL) THIOCARBONOHYDRAZONE,
   (h) 2-ACETYLPYRIDINE 5-((2-CHLOROPHENYL)CARBAMOYL) THIOCARBONOHYDRAZONE, and
   (i) 2-ACETYLPYRIDINE (5-(2-CHLOROANILINO)-1,3,4-THIADIAZOL-2-YL)HYDRAZONE.

4. A pharmaceutically acceptable salt of a compound of claim 3.

5. The compound 2-acetylpyridine-5-[(2-pyridylamino)thiocarbonyl]thiocarbonohydrazone.

6. A pharmaceutically acceptable salt of 2-acetylpyridine 5-[(2-pyridylamino)thiocarbonyl]thiocarbonohydrazone.

* * * * *

UNITED STATES PATENT AND TRADEMARK OFFICE
CERTIFICATE OF CORRECTION

PATENT NO. : 5,393,883

DATED : February 28, 1995

INVENTOR(S): Todd A. Blumenkopf, Thomas Spector, Devron R. Averett, Robert W. Morrision, Jr., Eric C. Bigham and Virgil L. Sytles It is certified that error appears in the above-identified patent and that said Letters Patent is hereby corrected as shown below:

Cover page to Patent, section [54], replace "Blumenhopf" with --Blumenkopf--

Signed and Sealed this

Ninth Day of May, 1995

Attest:

BRUCE LEHMAN

Attesting Officer     Commissioner of Patents and Trademarks